United States Patent
Copf, Jr.

(10) Patent No.: US 8,152,850 B2
(45) Date of Patent: Apr. 10, 2012

(54) INTERVERTEBRAL DISC PROSTHESIS

(75) Inventor: Franz Copf, Jr., Stuttgart (DE)

(73) Assignee: spontech spine intelligence group AG, Stuttgart (DE)

( * ) Notice: Subject to any disclaimer, the term of this patent is extended or adjusted under 35 U.S.C. 154(b) by 720 days.

(21) Appl. No.: 11/994,765

(22) PCT Filed: Jul. 6, 2006

(86) PCT No.: PCT/EP2006/006609
§ 371 (c)(1),
(2), (4) Date: Jun. 2, 2008

(87) PCT Pub. No.: WO2007/003438
PCT Pub. Date: Jan. 11, 2007

(65) Prior Publication Data
US 2009/0125111 A1  May 14, 2009

Related U.S. Application Data

(60) Provisional application No. 60/696,882, filed on Jul. 6, 2005, provisional application No. 60/741,817, filed on Dec. 2, 2005.

(30) Foreign Application Priority Data

Feb. 10, 2006 (EP) ................................. 06002765

(51) Int. Cl.
*A61F 2/44* (2006.01)
(52) U.S. Cl. ................................. 623/17.15
(58) Field of Classification Search ..... 623/17.11–17.16
See application file for complete search history.

(56) References Cited

U.S. PATENT DOCUMENTS

| 5,258,031 A | 11/1993 | Salib et al. |
| 5,370,697 A | 12/1994 | Baumgartner |
| 5,507,816 A | 4/1996 | Bullivant |
| 5,562,738 A | 10/1996 | Boyd et al. |
| 5,571,191 A * | 11/1996 | Fitz ............................ 623/17.11 |
| 5,676,701 A | 10/1997 | Yuan et al. |
| 6,290,726 B1 | 9/2001 | Pope et al. |

(Continued)

FOREIGN PATENT DOCUMENTS

DE  2 263 842  7/1974

(Continued)

OTHER PUBLICATIONS

Translation of International Patent Application Document No. WO 94/04100 to Mazda, Oct. 2005.*

(Continued)

*Primary Examiner* — Eduardo C Robert
*Assistant Examiner* — Summer Kostelnik
(74) *Attorney, Agent, or Firm* — Lempia Summerfield Katz LLC

(57) ABSTRACT

An intervertebral-disc prosthesis for insertion into an intervertebral disc compartment has a first and a second constituent element (10,10') each being provided on one side with a joint member (28,28') and on the other side with an abutment face which abuts against adjacent vertebrae. The abutment faces have a convexly curved region that has at least substantially the shape of a ramp. Preferably the region is surrounded by an annular flat region having a larger roughness than the curved region. The curved region may have a vertex which contacts a vertex of a dome formed in the adjacent vertebra. This facilitates rotation of the constituent element within the intervertebral disc compartment.

2 Claims, 19 Drawing Sheets

U.S. PATENT DOCUMENTS

| | | |
|---|---|---|
| 6,368,350 B1 | 4/2002 | Erickson et al. |
| 6,517,580 B1 | 2/2003 | Ramadan et al. |
| 6,936,071 B1 | 8/2005 | Marnay et al. |
| 7,001,432 B2 | 2/2006 | Keller et al. |
| 2003/0181981 A1 | 9/2003 | Lemaire |
| 2004/0068318 A1 | 4/2004 | Coates et al. |
| 2004/0127993 A1* | 7/2004 | Kast et al. ............ 623/17.16 |
| 2004/0158328 A1 | 8/2004 | Eisermann |
| 2004/0225362 A1 | 11/2004 | Richelsoph |
| 2005/0071007 A1 | 3/2005 | Malek |
| 2005/0085917 A1 | 4/2005 | Marnay et al. |
| 2005/0107881 A1* | 5/2005 | Alleyne et al. ......... 623/17.15 |
| 2005/0182491 A1 | 8/2005 | Ralph et al. |
| 2005/0192670 A1 | 9/2005 | Zubok et al. |
| 2005/0203626 A1 | 9/2005 | Sears et al. |
| 2005/0228500 A1 | 10/2005 | Kim et al. |
| 2005/0234553 A1 | 10/2005 | Gordon |
| 2005/0246024 A1 | 11/2005 | Zeegers |
| 2005/0256579 A1 | 11/2005 | Keller et al. |
| 2005/0267581 A1 | 12/2005 | Marnay et al. |
| 2006/0142862 A1 | 6/2006 | Diaz et al. |
| 2008/0133013 A1* | 6/2008 | Duggal et al. ......... 623/17.16 |

FOREIGN PATENT DOCUMENTS

| | | |
|---|---|---|
| DE | 35 29 761 | 7/1986 |
| DE | 0248018 | 7/1987 |
| DE | 203 20 454 | 10/2004 |
| DE | 103 61 166 | 7/2005 |
| EP | 333 990 | 9/1989 |
| EP | 566 810 | 10/1993 |
| EP | 754 018 | 2/1997 |
| EP | 1 188 423 | 2/2002 |
| EP | 1 236 352 | 2/2002 |
| EP | 1 475 059 | 11/2004 |
| EP | 1 523 962 | 4/2005 |
| EP | 1 532 948 | 5/2005 |
| FR | 2 632 516 | 12/1989 |
| FR | 2 694 882 | 2/1994 |
| FR | 2 718 635 | 10/1995 |
| FR | 2 742 653 | 6/1997 |
| FR | 2 805 733 | 9/2001 |
| WO | WO 94/04100 | 3/1994 |
| WO | WO 01/07893 | 2/2001 |
| WO | WO 01/64140 | 9/2001 |
| WO | WO 03/039400 | 5/2003 |
| WO | WO 03/090648 | 11/2003 |
| WO | WO 2004/034935 | 4/2004 |
| WO | WO 2005/004756 | 1/2005 |
| WO | WO 2005/053579 | 6/2005 |
| WO | WO 2005/060878 | 7/2005 |

OTHER PUBLICATIONS

International Search Report and Written Opinion from corresponding International application No. PCT/EP2006/006609 dated Jun. 6, 2006.

* cited by examiner

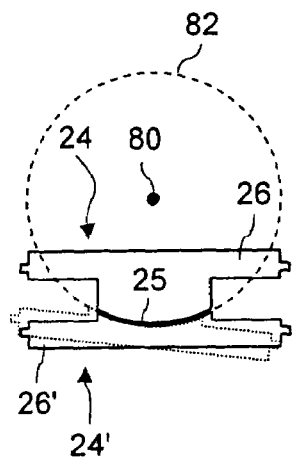
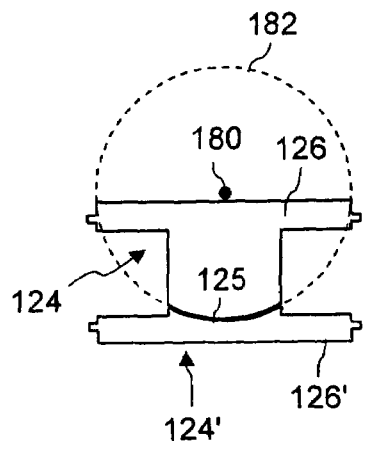
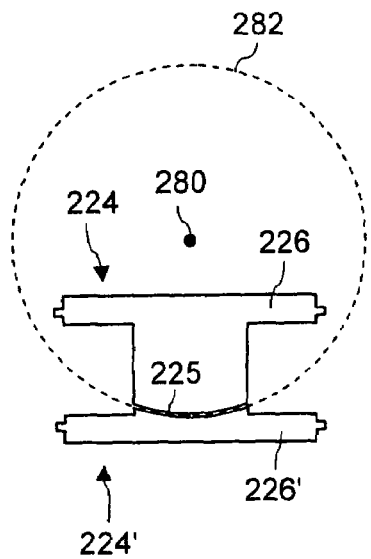
FIG. 15    FIG. 16    FIG. 17
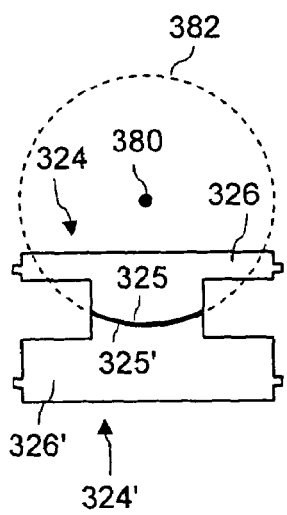
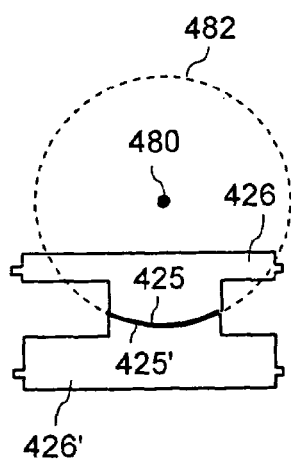
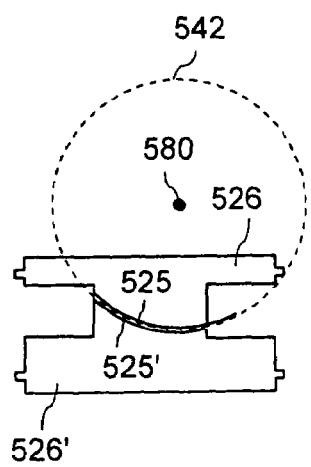
FIG. 18    FIG. 19    FIG. 20

INTERVERTEBRAL DISC PROSTHESIS

CROSS-REFERENCE TO RELATED APPLICATIONS

This US national phase application is based on international application no. PCT/EP2006/006609 filed on Jul. 6, 2006 and claims priority benefit of U.S. provisional application Ser. No. 60/696,882 filed Jul. 6, 2005 and Ser. No. 60/741,817 filed Dec. 2, 2005 and claims priority to European patent application EP 06002765.3 filed Feb. 10, 2006. The full disclosure of these earlier applications is incorporated herein by reference.

BACKGROUND OF THE INVENTION

1. Field of the Invention

The present invention relates to intervertebral disc prostheses for insertion into an intervertebral disc compartment which is formed between a first and a second vertebra. More particularly, the invention relates to intervertebral disc prostheses that restores the natural flexibility of the spine.

2. Description of Related Art

Intervertebral disc prostheses generally comprise two constituent elements each having a supporting plate that rests with an abutment face on an adjacent vertebra when the prosthesis is inserted into the intervertebral disc compartment. The other side of the respective supporting plate supports a joint member that allows a relative movement between the two supporting plates.

U.S. Pat. No. 6,936,071, which corresponds to WO 01/07893 A1, discloses an intervertebral disc prosthesis in which the upper supporting plate comprises a cap-shaped recess. The lower supporting plate is provided with a recessed compartment that receives an exchangeable slide-in insert having a cap-shaped projection. The cap-shaped recess in the upper supporting plate and the cap-shaped projection of the insert form a ball-and-socket joint so that the two supporting plates can be tilted relative to one another in all directions in space.

Before the intervertebral disc prosthesis is inserted into a cervical intervertebral disc compartment, the latter is usually machined in a material-abrading manner. During this procedure bone material is abraded with a milling cutter in order to create appropriately large and plane opposite surfaces on the adjoining vertebrae for the abutment faces of the supporting plates. Fins formed on the abutment faces of the supporting plates prevent slipping of the otherwise plane abutment faces on the adjacent vertebrae. The fins engage grooves which have previously been recessed into the adjoining vertebrae by chiseling. The precise milling of the grooves, however, is a relatively elaborate process. For that reason it is difficult to correctly position the prosthesis in the intervertebral disc compartment.

WO 2005/004756 A1 discloses an intervertebral disc prosthesis that does not comprise fins on the abutment faces. Instead, the abutment faces are slightly convexly curved in a manner that is adapted to the anatomic requirements of the intervertebral disc prosthesis. The geometric data of the healthy intervertebral disc compartment, in particular its height, are determined by extrapolation of data obtained from 3D scanning measurements performed on the diseased spine section. The convex curvature of the abutment faces is said to result in a self-centering effect of the supporting plates within the intervertebral disc compartment. The abutment faces are coated with hydroxyl apatit (HAK) ceramics or TCP materials. These coatings are usually porous and rough which ensures that the supporting plates do not slide within the intervertebral disc compartment.

With such abutment faces it is difficult to obtain both the desired self-centering effect and a durable fixation of the prosthesis in the intervertebral disc compartment. If the abutment faces have a coating with a smooth surface, the supporting plates slide within the intervertebral disc compartment. If the abutment faces have a coating with a rough surface, the friction is too large to obtain a self-centering effect.

EP 0 754 018 B1 discloses a similar intervertebral disc prosthesis. Here the center of motion of the prosthesis, i.e. the center of curvature of the aspherical ball-and-socket joint, is located in the posterior part of the prosthesis, but still between the supporting plates.

WO 03/090648 A1 discloses another prosthesis in which each supporting plate is configured to receive one insert. Each insert is provided with a cap-shaped recess. Both recesses commonly accommodate a ball enabling articulating movement between the supporting plates. The supporting plates have cylindrically curved abutment faces and flat wings arranged at the lateral sides of the supporting plates. Before the prosthesis can be inserted, the adjacent vertebrae have to be prepared by forming elongate recesses in the bone material. The shape of the recesses corresponds to the cylindrical shape of the abutment faces of the supporting plates. In order to prevent sliding movements of the supporting plates relative to the vertebrae along the cylinder axes, the wings are provided with teeth that improve the grip of the wings on the bone material.

Also with this prosthesis its positioning within the intervertebral disc compartment is solely determined by the skill of the surgeon who prepares the cylindrical recesses that accommodate the abutment faces of the supporting plates.

SUMMARY OF THE INVENTION

It is a first object of the present invention to provide an intervertebral disc prosthesis which is easy to implant into an intervertebral disc compartment and nevertheless remains fixedly in its implant position.

According to a first aspect of the invention, this object is achieved by an intervertebral disc prosthesis for insertion into an intervertebral disc compartment which is formed between a first vertebra and a second vertebra. The prosthesis comprises a first supporting plate which is provided on one side with a first joint member and has on the other side a first abutment face which abuts against the first vertebra when the intervertebral disc prosthesis is inserted into the intervertebral disc compartment. A second supporting plate is provided on one side with the second joint member and has on the other side a second abutment face which abuts the second vertebra when the intervertebral disc prosthesis is inserted into the intervertebral disc compartment. At least one of the first and second abutment faces has a convexly and aspherically curved region. According to the invention the curved region is completely surrounded by an annular flat region which has a rougher surface than the curved region.

The provision of a relatively smooth surface of the convexly curved region makes it possible that the prosthesis adjusts itself with respect to the domes by sliding movements when the intervertebral disc prosthesis is inserted into the intervertebral disc compartment. If the smooth surface is not rotationally symmetrical, but has a long and a short dimension in orthogonal directions, such a smooth surface even makes it possible that the intervertebral disc prosthesis may be inserted through a lateral access. A lateral access is often preferred because it does not require to push aside large and sensitive blood vessels that block the ventral access channel.

During insertion the intervertebral disc prosthesis is inserted through the access channel preferably with its long dimension parallel to the channel axis. After the intervertebral disc prosthesis has reached a position between the adjacent vertebrae, the pressure exerted by the vertebrae on the polished surface causes the prosthesis to rotate by about 45° to 90° (depending on the direction of the access channel) in the intervertebral disc compartment until it finally reaches its desired position with its long dimension extending laterally. Alternatively, operating means connected to the prosthesis are used to rotate the prosthesis within the intervertebral disc compartment.

The curved region is formed such that it, after having been inserted into the intervertebral disc compartment from a ventral or lateral access channel, further penetrates for some millimeters into the porous and relatively soft bone tissue (substantia spongiosa) between the tube of harder bone (substantia compacta). The annular ends of this hard tube will be referred to in the following as "apophyseal ring" of the vertebrae. The penetration is stopped when a flat and preferably rough region surrounding the convexly curved region rests on the apophyseal ring of the adjacent vertebra. This ensures a very tight and reliable connection of the intervertebral disc prosthesis to the adjacent vertebra.

In an advantageous embodiment the curved region of at least one abutment face is formed with a vertex point or vertex area being configured such that the constituent element is allowed to rotate within the adjacent dome by at least 10°, preferably by at least 25°, when the vertex of the curved region contacts a vertex of the dome. With abutment faces having exactly the shape of the dome, it is difficult for the surgeon to manually rotate the constituent elements with respect to the adjacent vertebra, because large curved faces are in immediate contact. If the abutment face is provided with such a vertex, however, only the vertices of the abutment faces and the domes contact each other before a more intimate connection is achieved after the abutment face has been pressed into the soft bone material within the dome.

Such a shape of the convexly curved region may require that the shape of the dome is biometrically determined prior to the insertion of the intervertebral disc prosthesis into the intervertebral disc compartment. This may be accomplished by computer processing high-resolution images of the vertebrae. The curved region is then machined or molded in accordance with the obtained biometrical shape data of the dome. However, since the shape of the curved region is preferably similar, but not identical to the geometry of the dome within the apophyseal ring, such an adaptation to the patient's specific geometry may in many cases not necessary. Instead, supporting plates that are fabricated on the basis of statistical data obtained for the affected vertebrae of many patients may be used.

There are many approaches to achieve a smooth surface of the curved region. For example, it may be polished or provided with a coating which has the desired surface properties. Preferably the surface has a arithmetic roughness Ra of less than 10 µm, preferably less than 1 µm which ensures that the kinetic friction coefficient is less than 0.1 with respect to the bone material.

Such properties may easily be achieved with the application of a diamond-like carbon coating (DLC) which is known in the art as such. Such coatings are biologically compatible, are very hard and have a low friction.

On the other hand, the flat region may have a kinetic friction coefficient of more than 1.0 with respect to the bone material of the apophyseal ring.

Of course, both of the supporting plates may also be formed in the manner described above.

According to another aspect of the invention, the above stated object is achieved by an intervertebral disc prosthesis for insertion into an intervertebral disc compartment which is formed between a first vertebra and second vertebra. The prosthesis comprises a first supporting plate which is provided on one side with a first joint member and has on the other side a first abutment face which abuts against the first vertebra when the intervertebral disc prosthesis is inserted into the intervertebral disc compartment. It further comprises a second supporting plate which is provided on one side with a second joint member and has on the other side a second abutment face which abuts the second vertebra when the intervertebral disc prosthesis is inserted into the intervertebral disc compartment. At least one of the first and second abutment faces has a convexly curved region. According to the invention the convexly curved region has (at least substantially) the case of a ramp.

It has been discovered that such a shape is similar to the geometry of the dome that accommodates the curved region if the supporting plate with the curved region is implanted. Since the ramp is not rotationally symmetrical, a self-centering torque is produced if there is a compressive force applied between the vertebra and the supporting plate. During the implant surgery this force is produced by ligaments that extend along the spine. When the supporting plate has rotated to a position where these compressive forces are symmetrical, the torque vanishes and the rotation ceases accordingly. If the compressive force applies still further, the ramp-shaped curved region will press into the bone material (substantia spongiosa) within the apophyseal ring, thereby causing a partial deformation of the bone material. This ensures a very intimate contact between the bone material and the curved.

Even if the implant of an intervertebral disc prosthesis has been performed without any complications, it may nevertheless sometimes be necessary to change the joint members that determine the location of the center of motion. Usually the prosthesis will be implanted through a ventral access. However, creating such a ventral access for a second time is often associated with increased risks due scars caused by the former surgery.

It is therefore another object of the present invention to provide an intervertebral disc prosthesis that reduces such risks.

According to the invention, this object is achieved by an intervertebral disc prosthesis for insertion into an intervertebral disc compartment which is formed between a first and a second vertebra. The prosthesis comprises a first supporting plate having a longitudinal side and a transfer side, a first slide-in compartment on the first supporting plate, a first joint-member which is separately connected to the first supporting plate and comprises a first slide-in plate which is capable of being inserted into the first slide-in compartment. The prosthesis further comprises a second supporting plate which supports a second joint member. According to the invention, the first slide-in plate and the first slide-in compartment are configured such that the first slide-in plate is capable of being inserted into the first slide-in compartment both from the longitudinal side and from the transfer side of the first supporting plate.

This makes it possible to exchange the first joint element from a lateral access channel. Any risks associated with providing a ventral access channel for a second time are thus avoided.

The inventor has discovered that many of the problems encountered with conventional intervertebral discs prosthesis are a result of a mismatch between the anatomically possible movements of the vertebrae on the one hand and the movements made possible by the prosthesis. If this mismatch is substantial, the muscles and ligaments supporting the spine are naturally strained, which results in tenseness and finally in pain.

It is therefore a further object of the present invention to provide an intervertebral disc prosthesis which reduces this mismatch considerably.

According to the invention this object is achieved by an intervertebral disc prosthesis for insertion into an intervertebral disc compartment which is formed between an upper and a lower vertebra. The prosthesis comprises a first joint member that is associated with the upper vertebra. A second joint member is associated with the lower vertebra and is configured such that it is capable of swiveling relative to the first joint member around a swivel point or swivel axis. According to the invention the swivel point or swivel axis is positioned above the second joint member and preferably above the first joint member. In many cases it may even be advantageous to position this swivel point or swivel axis above a supporting plate that supports on one side the first joint member and has on the other side a first abutment face which abuts against the first vertebra when the intervertebral disc prosthesis is inserted into the intervertebral disc compartment.

In conventional prostheses, the swivel point is positioned within or below the lower joint member. However, it has been discovered that the center of motion is not below, but (significantly) above the lower joint member. For example, in the case of lumbar vertebrae the center of motion is in the apex of the dome that is surrounded by the apophyseal ring of the upper vertebra. Only if the swivel point or swivel axis of the prosthesis substantially coincides with the anatomical center of motion, the elements of the prosthesis will swivel to an extent as it is the case if a natural and healthy intervertebral disc is in the intervertebral disc compartment. As a result, unnatural strain of ligaments and muscles are avoided, and a stiffening of the prosthesis will not occur.

In order to be able to position the swivel point or swivel axis as close as possible to the natural center of motion of the adjacent vertebrae, the position and curvatures of the joint elements have to be carefully selected. For that reason the prosthesis may be assembled like a construction kit from a plurality of components of the same kind, but having different dimensions or curvatures. This makes it possible that the surgeon assembles the prosthesis during the implant surgery when he is able to determine how much bone material has to be removed from the adjacent vertebra. As a matter of course, the assembly of the prosthesis from a variety of different components is also advantageous if no or only a small amount of bone material has to be removed, as is it often the case with lumbar vertebrae, or if it is clear in advance how much bone material has to be removed. In these cases the components are determined on the basis of preoperative 3D scans such that the swivel point or swivel axis will be as close as possible to the natural center of motion of the adjacent vertebrae.

Such a construction kit may comprise first and second joint members having a different shape (curvatures and/or spacings from base surfaces), and/or different supporting plates and/or a set of different spaces having the shapes of discs or wedges that can be inserted between the supporting plates and the adjacent vertebrae.

A further problem with the known intervertebral disc prostheses described further above consists in the fact that the mobility of the supporting plates in the event of a lateral tilting of the vertebrae about a tilt axis parallel to the transverse sides of the supporting plates is limited only by the fact that the edges of the supporting plates strike one another in the case of a relatively large tilt angle. Occasionally it is also desirable to be able to limit the tilt angle of the supporting plates towards the front and/or towards the back selectively.

For this reason it is a further object of the invention to provide an intervertebral disc prosthesis in which tilt angles can be limited in a straightforward manner.

According to the invention this object is achieved by an intervertebral disc prosthesis for insertion into an intervertebral disc compartment which is formed between a first and a second vertebra. The prosthesis comprises a first supporting plate supporting a first joint member and a second supporting plate supporting a second joint member. The second joint member cooperates with the first joint member so as to allow a tilting or swiveling movement between the first and second supporting plates. A projection is arranged on the first supporting plate which serves as a stop that restricts the relative tilting or swiveling movement between the first and second supporting plates. According to the invention the projection is arranged on an exchangeable guide-plate which is capable of being inserted into the guide-plate slide-in compartment provided on the first supporting plate.

By providing one or more projections on guide-plates it is possible to easily exchange the projections by merely removing a guide-plate and inserting another guide-plate having a different projection. Since the insertion into a slide-in compartment requires only a translational movement, such an exchange may be carried out through a very small access channel if the orientation of the slide-in compartment is appropriately selected with respect to the possible orientations of access channels. Often a lateral access is preferable once an intervertebral disc prosthesis has been implanted. For that reason the slide-in compartments should be oriented such that the guide-in plate supporting the projection can be drawn out the slide-in compartment with a lateral movement.

A limitation of the lateral tilt angles is achieved if the first projection is arranged between the first joint member and a transverse side of the first supporting plate. If the tilt angle of the supporting plates towards the front and/or towards the back is to be limited, the projection should be arranged between the first joint member and a longitudinal side of the first supporting plate.

A further problem with the known intervertebral disc prostheses is that a relatively large ventral access canal has to be prepared for the insertion of the supporting plates.

For this reason, a further object of the present invention is to provide an intervertebral disc prosthesis that can be inserted into the intervertebral disc compartment through a smaller ventral access canal.

This object is achieved by means of an intervertebral disc prosthesis comprising a first supporting plate which supports a first joint member and with a second supporting plate which supports a second joint member. According to the invention, the first supporting plate comprises connecting elements for separably connecting the first supporting plate to an operating means with which the first supporting plate can be rotated about an axis that is substantially perpendicular to the first supporting plate.

In this way, the first supporting plate, with its short transverse side pointing forward, can be introduced through a narrower ventral access canal having a diameter that is given not by the length of the long sides, but by the length of the short narrow transverse sides of the supporting plates. The supporting plate is firstly rotated into the definitive position in, or in the vicinity of, the intervertebral disc compartment with the aid of the operating means. The smaller the diameter of the access canal, the lower is the risk of damage to blood vessels that have to be displaced when the ventral access canal is being created.

BRIEF DESCRIPTION OF THE DRAWINGS

Various features and advantages of the present invention may be more readily understood with reference to the following detailed description taken in conjunction with the accompanying drawing in which:

FIG. 15 shows the joint elements of the two constituent elements in a first configuration;

FIG. 16 shows the joint elements of the two constituent elements in a second configuration;

FIG. 17 shows the joint elements of the two constituent elements in a third configuration;

FIG. 18 shows the joint elements of the two constituent elements in a fourth configuration;

FIG. 19 shows the joint elements of the two constituent elements in a fifth configuration;

FIG. 20 shows the joint elements of the two constituent elements in a sixths configuration;

DETAILED DESCRIPTION OF PREFERRED EMBODIMENTS

Figure 1:
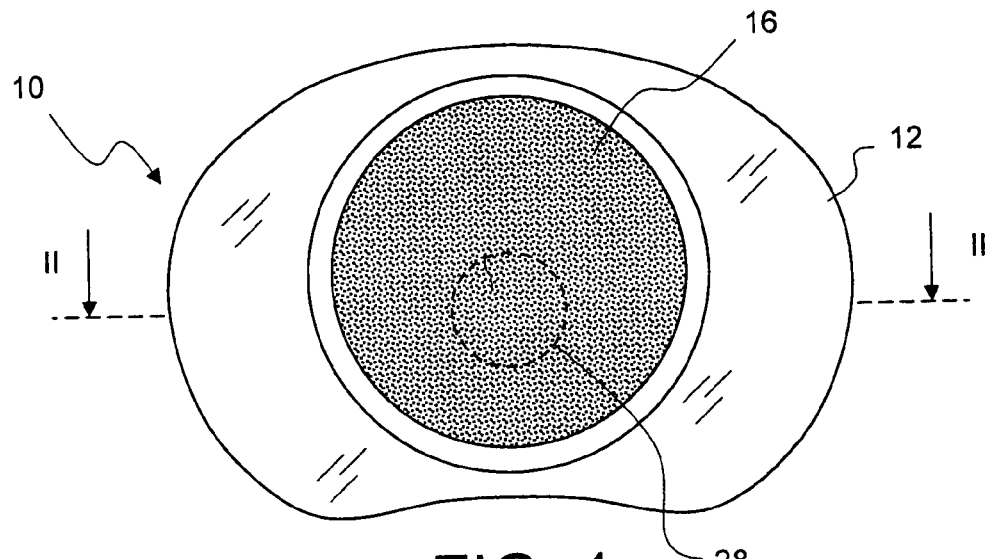
FIG. 1 is a top view of an upper constituent element of an intervertebral disc prosthesis according to the invention.

FIGS. 1 to 5 show an upper constituent element of an intervertebral disc prosthesis in a top view, in a section along line II-II, in a bottom view, in a section along line IV-IV, and in a section along line V-V, respectively.

The upper constituent element denoted in its entirety by 10 comprises an upper supporting plate 12 having a periphery that is approximately kidney-shaped. Into a central recess 14 (see FIG. 2) on the upper side of the upper supporting plate 12 a spherical-cap insert 16 is inserted and is held there by a latching ring 18 which is formed on the spherical-cap insert 16. In the exemplary embodiment shown the outward-pointing external surface, denoted by 20, of the spherical-cap insert 16 is curved in spherically convex manner. However, inserts with aspherical convex caps may be used as well, as is described further below with reference to FIGS. 24 to 27. The external surface 20 of the spherical-cap insert 16 supports a coating 22 that has a high degree of roughness.

In the exemplary embodiment shown the spherical-cap insert 16 consists of a relatively soft and elastic material, for example an elastomer, whereas the surrounding upper supporting plate 12 is manufactured from a harder material, for example a metal such as titanium. After the insertion of the upper constituent element into an intervertebral disc compartment, the spherical-cap insert 16 sits close, with its rough coating 22, on the relatively soft material which is located within the apophyseal ring of the adjacent vertebra. The surrounding harder region denoted by 23 on the outward-pointing side of the upper supporting plate 12 is supported on the apophyseal ring of the adjacent vertebra.

On the underside of the upper supporting plate 12 situated opposite the spherical-cap insert 16 there is a joint element 24 which comprises a slide-in plate 26 with a convex spherical-cap joint 28 integrally molded thereon. Parallel to the transverse sides of the upper supporting plate 12 there extend guide ribs 30, 32 which are molded on the slide-in plate 26. Due to the convex curvature of the spherical-cap joint 28, the center of motion is positioned above the joint. This has substantial advantages at least for prostheses inserted in lumbar intervertebral compartments, as will be explained in more detail below.

In the direction towards the transverse sides of the upper supporting plate 12 the joint element 24 adjoins a first guide plate 34 and a second guide plate 36. The two guide plates 34, 36, which in principle are of similar construction, bear a first and a second projection 38, 40, respectively, which are of parallelipipedal design and which serve as stops for the purpose of limiting the movement of the joint. In the direction towards the joint element 24 the guide plates 34, 36 are provided with guide grooves 42, 44 which are engaged by the guide ribs 30, 32 of the slide-in plate 26 of the joint element 24.

Figure 5:
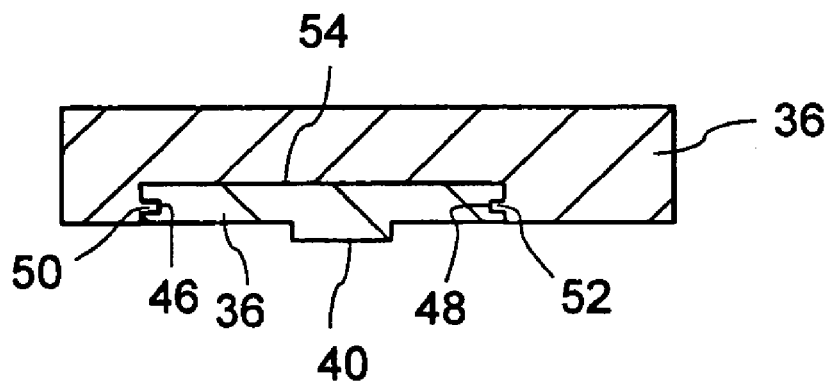
FIG. 5 is a section along line V-V of the upper constituent element shown in FIG. 1.

As can be discerned in the sectional representation along line V-V shown in FIG. 5, in the direction towards the longitudinal sides of the upper supporting plate 12 the two guide plates 34, 36 are likewise provided with guide grooves 46, 48 which are of a design that is complementary to guide ribs 50, 52 which are formed on the upper supporting plate 12.

In FIG. 5 it can further be discerned that the second guide plate 36 is received in a second guide-plate slide-in compartment 54 which is open only in the direction towards the middle of the upper supporting plate 12. The second guide plate 36 can consequently be inserted from the side into the second guide-plate slide-in compartment 54, with the guide grooves 46, 48 of the second guide plate 36 engaging the guide ribs 50, 52 of the upper supporting plate 12. The front side of the second guide plate 36, on which the guide groove 44 is formed, finally strikes a stop 55 which is formed on the upper supporting plate 12 (see FIG. 3). In this way, the position of the second guide plate 36 in the second guide-plate slide-in compartment 54 is defined by abutment in all directions other than the slide-in direction.

In order to prevent an unintentional slipping of the second guide plate 36 out of the second guide-plate slide-in compartment 54, the second guide plate 36 is preferably manufactured from a material that has elastic properties. Polyvinyl chloride, for example, may be envisaged for this purpose. The frictional resistance between the second guide plate 36 and the upper supporting plate 12 should be such that the second guide plate 36 can be inserted into the second guide-plate slide-in compartment 54 by hand or with the aid of a tool but cannot be redetached from the second guide-plate slide-in compartment 54 without the aid of a tool after the insertion of the intervertebral disc prosthesis into the intervertebral disc compartment.

Figure 2:
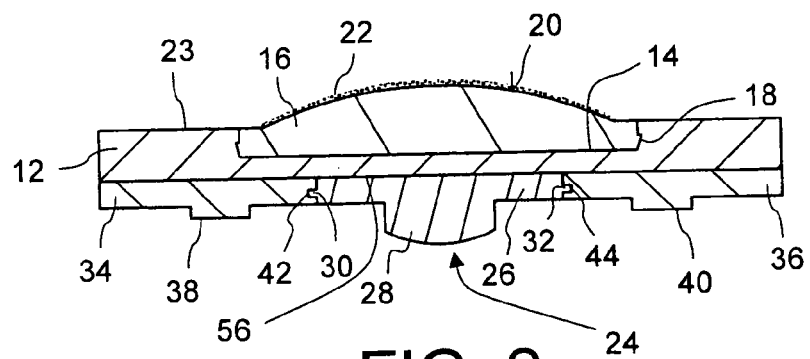
FIG. 2 is a section along line II-II of the upper constituent element shown in FIG. 1.
Figure 3:
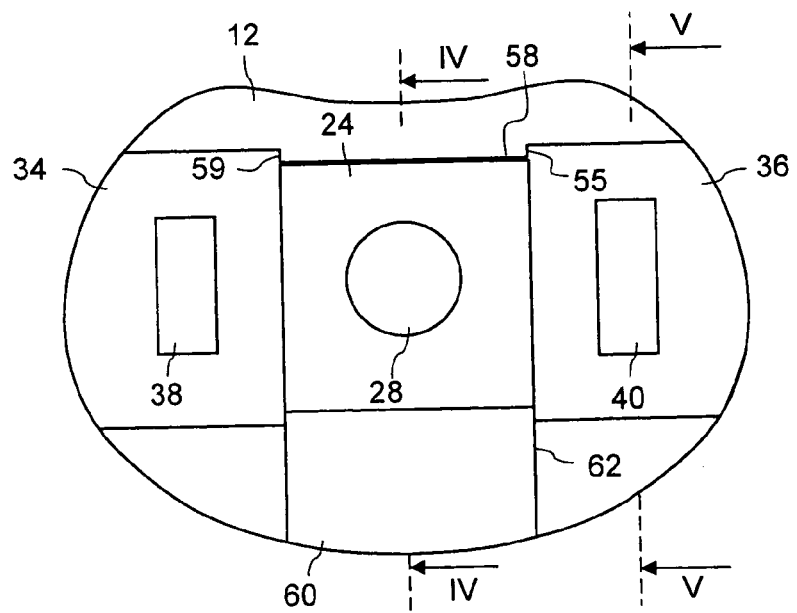
FIG. 3 is a bottom view of the upper constituent element shown in FIG. 1.
Figure 4:
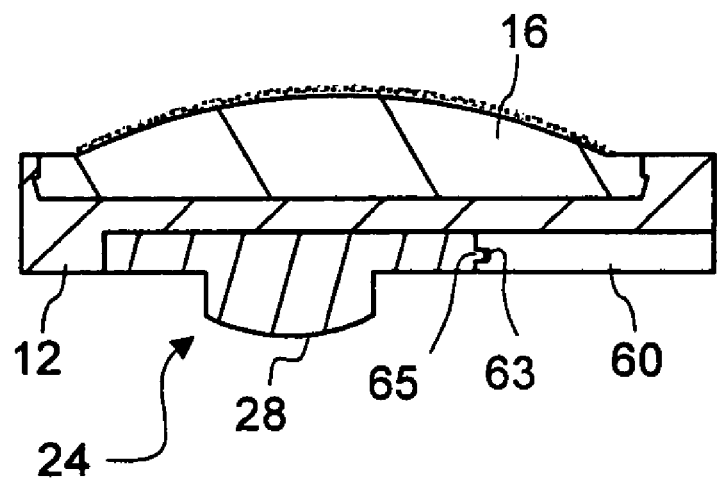
FIG. 4 is a section along line IV-IV of the upper constituent element shown in FIG. 1.

As FIGS. 1 to 3 show, the upper constituent element 10 is formed symmetrically relative to a plane of symmetry passing through the middle of the spherical-cap insert 16 and of the spherical-cap joint 28. The first guide plate 34 is consequently constructed in the same way as the second guide plate 36, and thus the above remarks apply correspondingly to the second guide plate 36.

The side faces of the two guide plates 34, 36 pointing towards the middle define a slide-in compartment 56 for the joint element 24 along the transverse sides of the upper supporting plate 12. Along the longitudinal sides of the upper supporting plate 12, the slide-in compartment 56 is delimited, on one side, by a step 58 which is formed on the upper supporting plate 12 (cf. FIG. 3) and, on the longitudinal side situated opposite, by a third guide plate 60. The third guide plate 60 is inserted into a third guide-plate slide-in compartment 62 which is formed on the underside of the upper supporting plate 12. The side of the front guide plate 60 pointing towards the middle of the supporting plate 12 is, as can be discerned in FIG. 4, likewise provided with a guide groove 63 which is engaged by a guide rib 65, of complementary shape, pertaining to the slide-in plate 26 of the joint element 24.

In this way, the slide-in plate 26 of the joint element 24 bears on three sides against the guide plates 34, 36 and 60 and on the fourth side against the step 58 and is consequently fixed on the underside of the upper supporting plate 12 in all directions.

Figure 6A:
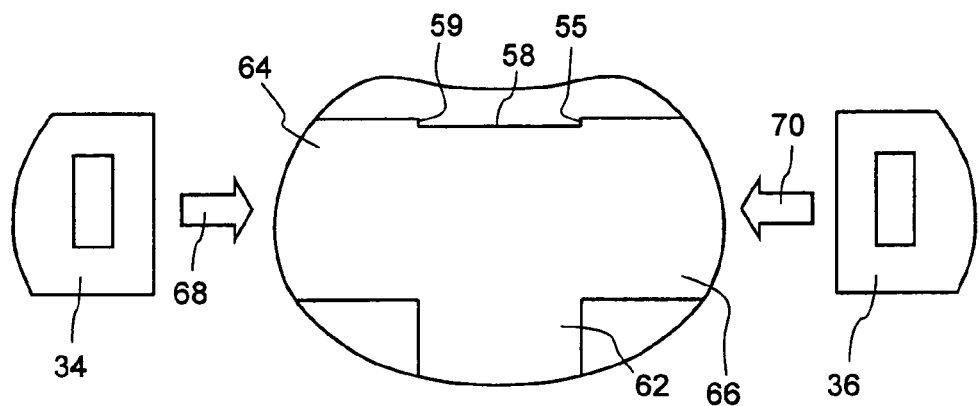
FIGS. 6a to 6c show the underside of the upper supporting plate in several states during the assembly of the upper constituent element.
Figures 6B, 6C:
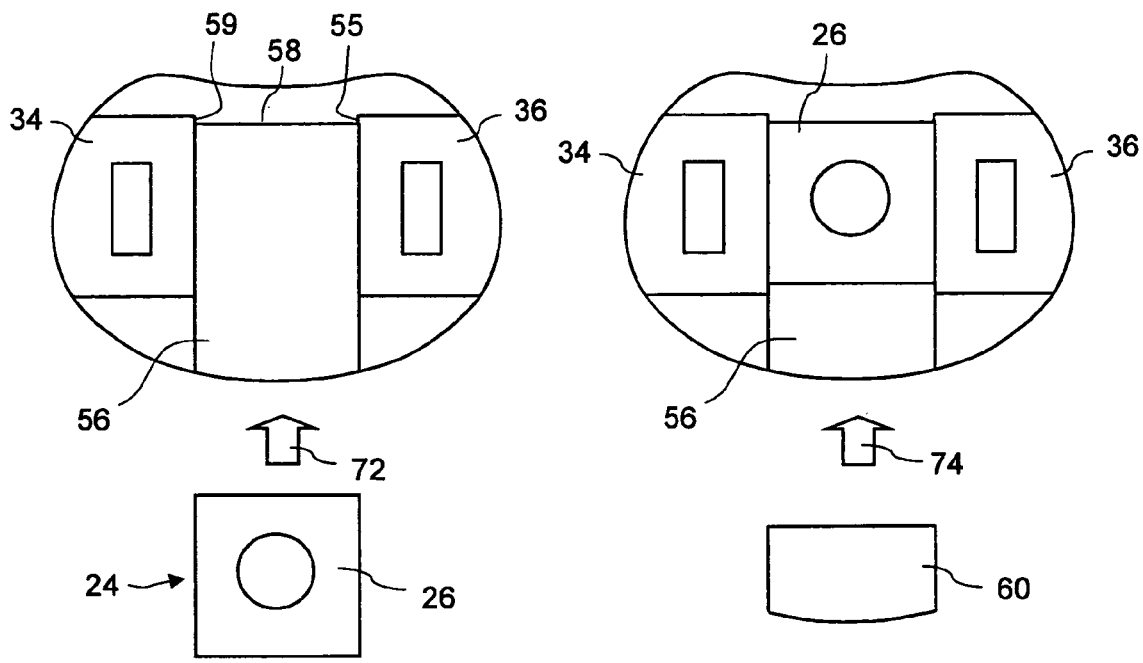

In FIGS. 6a to 6c the assembly of the upper constituent element 10 is elucidated in several stages in a simplified schematic representation.

In FIG. 6a the underside of the upper supporting plate 12 is shown without the guide plates 34, 36, 60 and the joint element 24. In this representation, lateral guide-plate slide-in compartments 64, 66 for the first and second guide plates 34, 36, respectively, and also the third guide-plate slide-in compartment 62 for the third guide plate 60 can be discerned. As indicated by arrows 68, 70, the first and second guide plates 34, 36 are now inserted from the side into the guide-plate slide-in compartments 64 and 66, respectively, until they strike the stops 55, 59.

This state is shown in FIG. 6b. The lateral guide plates 34, 36 now form, together with the step 58, the slide-in compartment 56 for the slide-in plate 26 of the joint element 24. The slide-in plate 26 is now inserted into the slide-in compartment 56 from the front, as indicated by an arrow 72. In order to secure the joint element 24 against unintentional slipping out of the slide-in compartment 56, the third guide plate 60 is now also inserted into the slide-in compartment 56 from the front, as indicated in FIG. 6c by an arrow 74.

The modular structure, described above, of the upper constituent element 10 permits the joint element 24 and the first and second guide plates 34, 36 with the projections 38 and 40, respectively, serving as stops to be assembled practically arbitrarily in the manner of a construction kit. Furthermore, an exchange of the guide plates 34, 36 and of the joint element 24 is possible even after the intervertebral disc prosthesis has been surgically inserted into the intervertebral disc compartment. This will be elucidated in more detail further below with reference to FIGS. 12 to 19.

Figure 7:
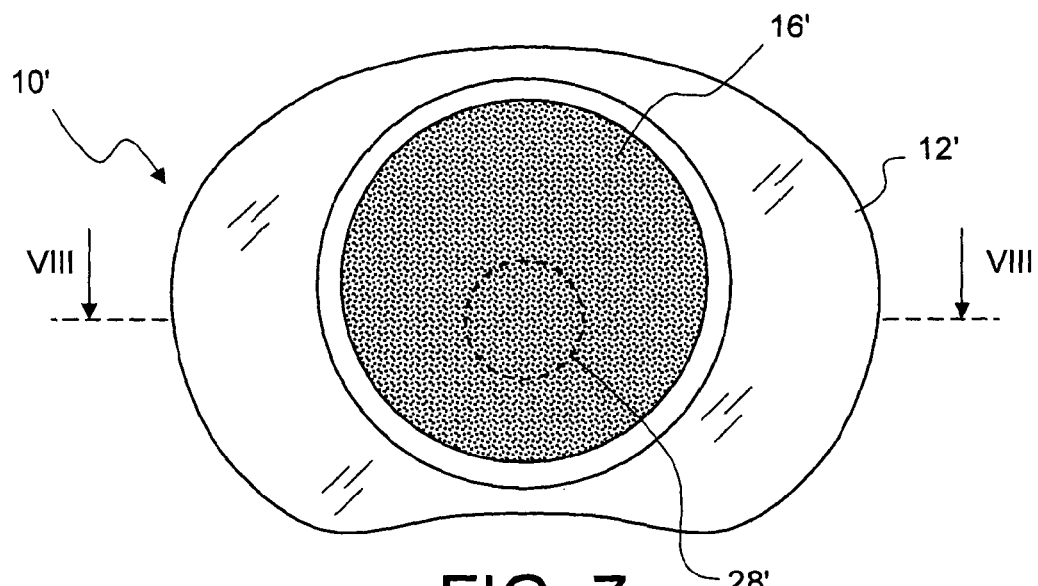
FIG. 7 is a top view of a lower constituent element of an intervertebral disc prosthesis according to the invention.
Figure 8:
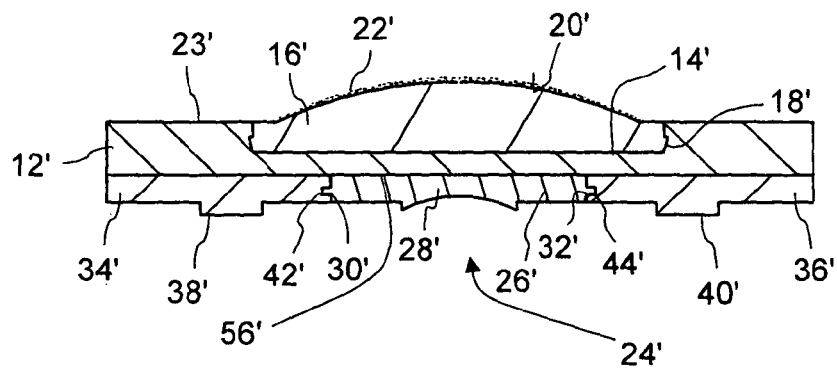
FIG. 8 is a section along line VIII-VIII of the lower constituent element shown in FIG. 7.
Figure 9:
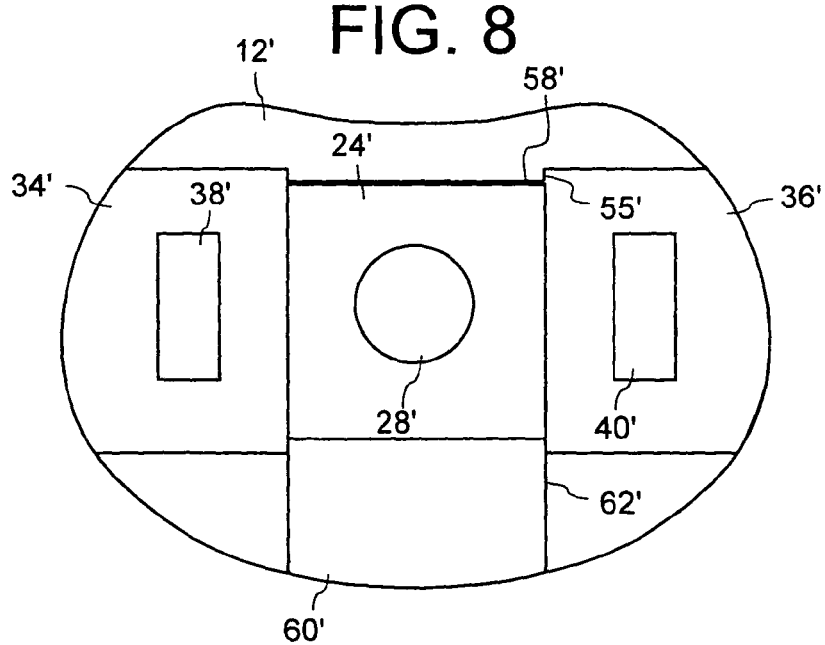
FIG. 9 is a bottom view of the lower constituent element shown in FIG. 7.

FIGS. 7 to 9 show, in representations similar to FIGS. 1 to 3, a top view, a section along line VIII-VIII, and a bottom view of a lower constituent element 10' which together with the upper constituent element forms the intervertebral disc prosthesis. The lower constituent element 10' differs from the upper constituent element 10 merely in that the convex spherical-cap joint 28 has been replaced by a concave spherical-cap joint 28'. The curvatures of the convex spherical-cap joint 28 and of the concave spherical-cap joint 28' are numerically equal, so the two spherical-cap joint 28, 28' together form a ball-and-socket joint.

Since the two constituent elements 10, 10' are otherwise of identical construction, reference may to this extent be made to the description of the upper constituent element 10. In order to make parts of the upper constituent element 10 and of the lower constituent element 10' corresponding to one another distinguishable, the parts of the lower constituent element 10' are labeled with dashed reference numerals.

Figure 10:
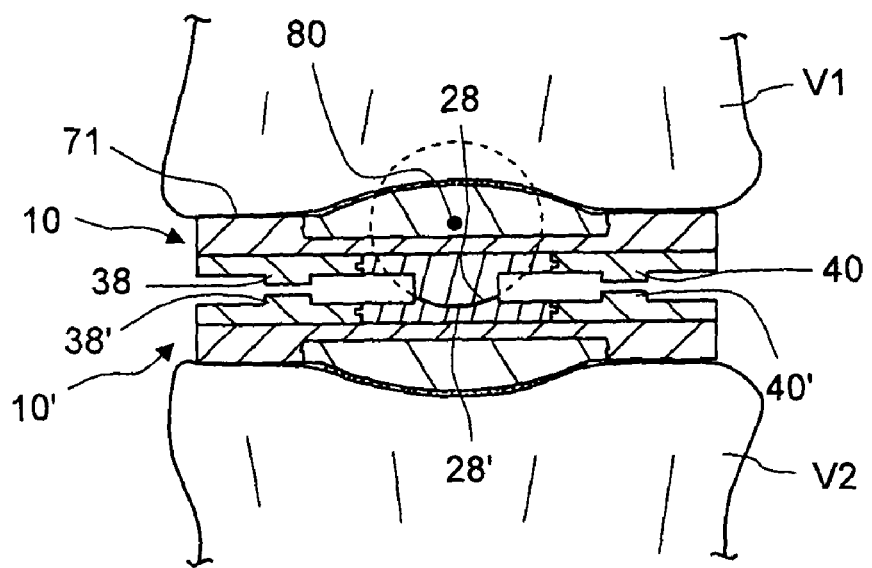
FIG. 10 is a side view of the intervertebral disc prosthesis in the inserted state.

FIG. 10 shows an intervertebral disc prosthesis constructed from the two constituent elements 10, 10' after its positioning in an intervertebral disc compartment. In FIG. 10 it can be readily discerned that the relatively soft and elastic spherical-cap insert 16 with the rough coating 22 bears against the likewise soft material that is located within the apophyseal ring of an upper vertebra V1. In this way, a very intimate connection is achieved between the spherical-cap insert 16 and the soft material of the vertebra V1. The roughness of the coating 22 has the effect that the upper constituent element is unable to slip within the intervertebral disc compartment.

The harder region of the upper supporting plate 12 surrounding the spherical-cap insert 16 is supported on the apophyseal ring 71 of the vertebra V1. Via the harder region, the large longitudinal forces are transmitted between the vertebra V1 and the upper constituent element 10. Corresponding remarks apply in respect of the lower constituent element 10', which rests on the lower vertebra V2.

Figure 11:
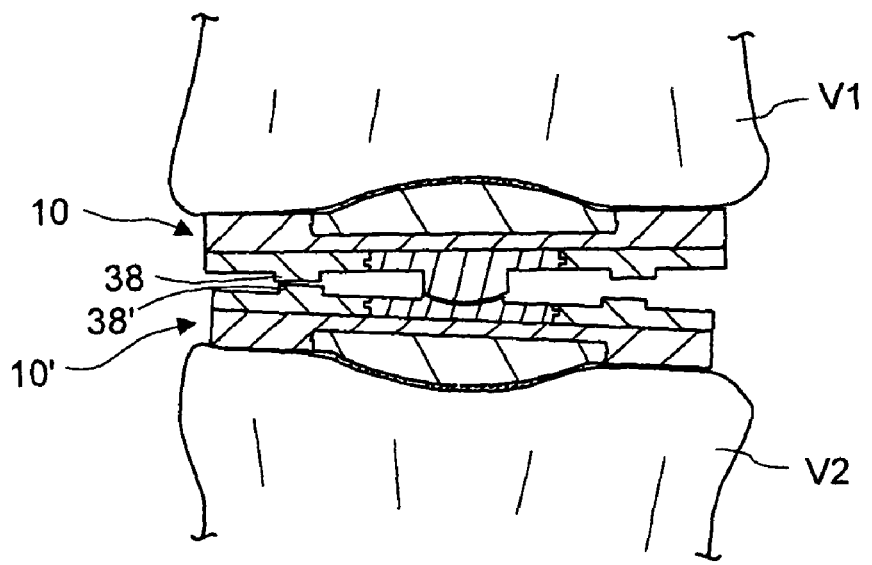
FIG. 11 is a side view of the intervertebral disc prosthesis corresponding to FIG. 10 but with constituent elements tilted relative to one another.

In the inserted state the convex spherical-cap joint 28 of the upper constituent element 10 rests on the concave spherical-cap joint 28' of the lower constituent element 10', so that the two constituent elements 10, 10' can be swiveled in all directions relative to one another about a swivel point 80 whose significance will be described in more detail below. Since a swiveling of the vertebrae V1, V2 in the lateral direction is generally intended to be possible only to a limited extent, the projections 38, 40 on the guide plates 34, 36 of the upper constituent element 10 and also the corresponding projections 38', 40' on the guide plates 34', 36' of the lower constituent element 10' are constructed in such a way that the two constituent elements 10, 10' can only be swiveled by a few degrees about an axis perpendicular to the plane of the paper. In FIG. 11 it is shown how the projections 38, 38' limit a swiveling movement to a maximal swivel angle of about 4°. It should be noted that it may suffice to provide only one of the constituent elements 10, 10' with projections.

As can be seen in FIGS. 3 and 9, the projections 38, 40 and 38', 40' have a rectangular base area, with the long side extending in a dorsal-ventral direction. This shape ensures also a limitation of swiveling movements forward and backward. The length of the long side determines the maximum swivel angle in this direction which may be in the range between 6° and 12°. With projections 38, 40 and 38', 40' having a substantially quadratic base area, no limitation of such swivel movements is achieved, which may be desirable under certain circumstances.

If the maximal swivel angle for one or both swivel axes is to be changed, it is sufficient to exchange either the upper guide plates 34, 36, the lower guide plates 34', 36', or all four guide plates 34, 36, 34', 36' for guide plates that are provided with different projections. In this case the projections 38, 40 and 38', 40' either may have a different height, a different base area or may be arranged closer to, or further away from, the joint elements 24, 24', for example. It should be noted that such changes of the swivel angles are possible even after the disc prosthesis has been inserted into the intervertebral compartment. This is because the guide plates 34, 36, 34', 36' can be replaced through lateral accesses without the need to remove the entire prosthesis.

Figure 12:
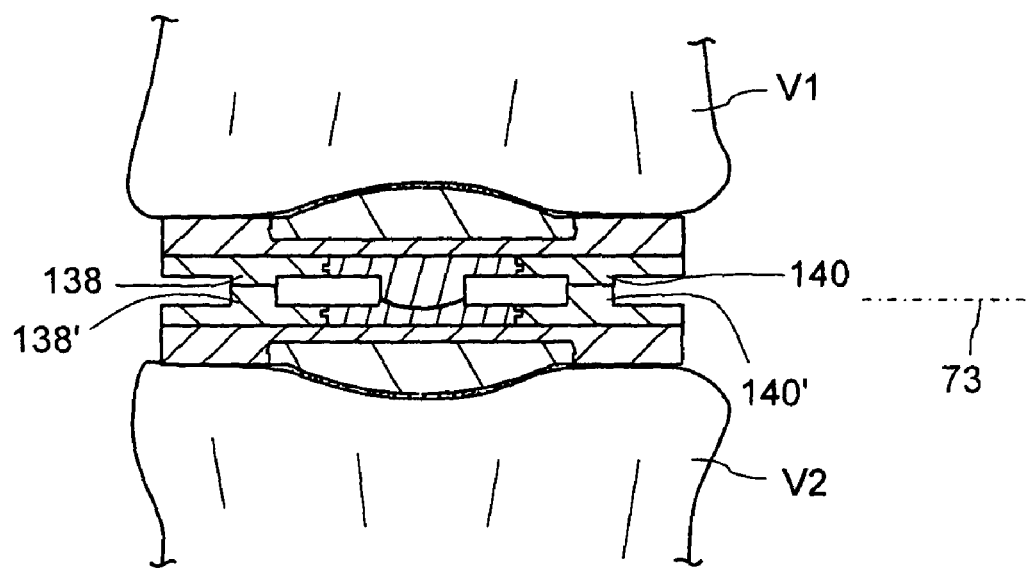
FIG. 12 is a side view of an intervertebral disc prosthesis, corresponding to FIG. 10, which has been fixed so as to counter lateral tilting movements.

FIG. 12 shows a representation corresponding to FIGS. 10 and 11, in which guide plates 134, 136, 134', 136' have been inserted into the upper and lower supporting plates 12, 12', respectively, the projections of which, 138, 140 and 138', 140', respectively, totally fix the intervertebral disc prosthesis. For this purpose the projections 138, 140, 138', 140' may have relatively large-area and flat bearing faces in order to achieve a good distribution of forces. If the intervertebral disc prosthesis is to be fixed merely in the lateral direction, but swiveling movements towards the front and towards the rear are to continue to be possible, the projections 138, 140, 138', 140' may take the form of transversely situated semicylinders. The semicylinders are then able to roll onto one another, so that a swiveling of the two constituent elements 10, 10' is possible about a swivel axis which is indicated in FIG. 12 by 73.

In order to limit the maximal swivel angle for swiveling movements in the forward direction, one or both third guide plates 60, 60' may also be provided with projections which serve as stops. However, the provision of the third guide plates 60, 60' with projections may not be preferred if the projections shall be replaceable. This is because the guide plates 60, 60' can only be exchanged through a ventral access canal, and the preparation of such a canal for a second time is often a difficult and risky process.

Figure 13:
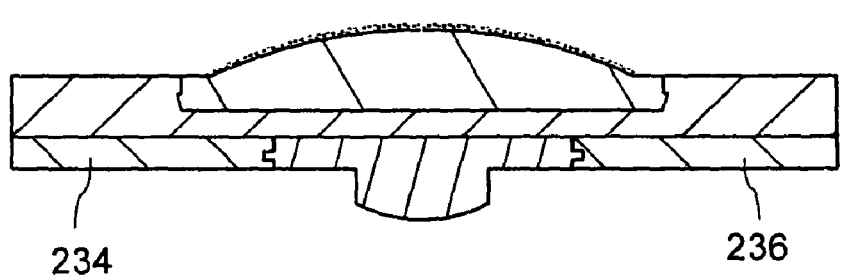
FIG. 13 is a representation, corresponding to FIG. 2, of a variant without projections serving as stops.

Of course, the stops limiting the mobility may also be dispensed with altogether. In this case, use is made of guide plates 234, 236 without projections. FIG. 13 shows such an embodiment in a sectional representation similar to FIG. 2.

It is to be understood that the intervertebral disc prosthesis described above can also be inserted into an intervertebral disc compartment the other way round, so that the upper constituent element 10 adjoins the lower vertebra V2 and the lower constituent element 10' adjoins the upper vertebra V1.

Since the joint elements 24, 24' of the two constituent elements 10, 10' are exchangeable in a straightforward manner, the intervertebral disc prosthesis can be adapted within very wide limits to the respective shape of the intervertebral disc compartment and to the possible movements of the vertebrae V1, V2 adjoining it.

The shape of the intervertebral disc compartment usually varies depending on the longitudinal position of the adjacent vertebrae in the human spine. Often, however, the size of the compartment has to be substantially enlarged by abrasive methods, for example for removing pathological deformations in the vicinity of an apophyseal ring of one or both adjacent vertebra.

The possible movements of the vertebrae are anatomically predetermined by the facet joints, the joint capsules, the annulus fibrosus and the ligaments that extend along the spine. The inventor has discovered that many of the problems encountered with conventional intervertebral disc prostheses are a result of a mismatch between the anatomically possible movements of the vertebrae on the one hand and the movements made possible by the prosthesis. If this mismatch is substantial, the muscles and ligaments supporting the spine are unnaturally strained, which results in tenseness and finally in pain. Further, it has been found out that the movements of a pair of adjacent vertebrae may be described, at least to a very good approximation, as a swiveling movement in which the lower vertebra is swiveled around a swivel point that is associated with the upper vertebra.

For the purpose of describing the possible movements, use will be made in the following of the term 'center of motion', which denotes the swivel point of this movement. For cervical vertebrae, the center of motion of the vertebrae is a few millimeters away from the upper vertebral face which delimits the intervertebral disc compartment. Recent researches carried out by the inventor have shown, however, that this generally does not apply for the lumbar vertebrae. With these, the center of motion is positioned almost exactly in the apex of the lower dome of the upper lumbar vertebra.

Figure 14:
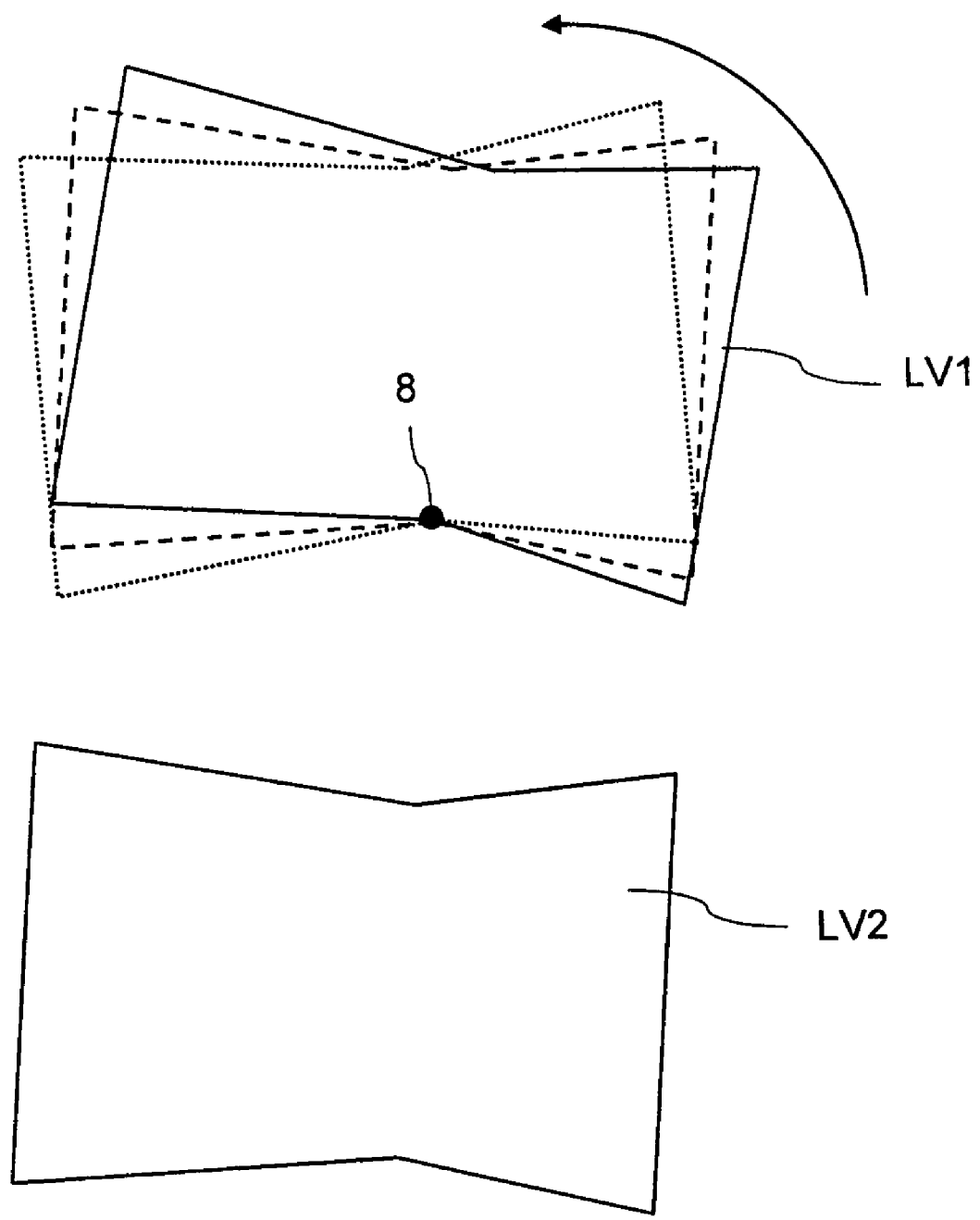
FIG. 14 is a schematic simplified sectional view of an upper and a lower lumbar vertebra.

FIG. 14 shows in a schematic simplified sectional view an upper and a lower lumbar vertebra LV1 and LV2, respectively, having domes that are approximated in the sectional view by corners formed by straight lines. The possible movements of the upper lumbar vertebra LV1 is indicated in FIG. 14 by different broken lines. In this representation the center of motion, which is denoted by reference numeral 8, is situated in the corner formed by the two straight lines of the lower corner of the upper lumbar vertebra LV1. This corner corresponds to the apex of the curved dome of a real upper lumbar vertebra. From the foregoing it becomes clear that an intervertebral disc prosthesis for a lumbar intervertebral disc compartment should be configured such that its center of motion is positioned as close as possible to the apex of the lower dome of the upper vertebra. With the prosthesis described above this may easily be achieved by inserting joint elements 24, 24' having the required shape.

How it is possible to attain almost any arbitrary center of motion with the prosthesis described above will now be explained in more detail with reference to FIGS. 15 to 18.

In FIG. 15 the two joint elements 24, 24' of the two constituent elements 10 and 10', respectively, are represented in isolated manner. The center of motion, which is denoted by 80, is the center of a dashed circle 82 having a segment that coincides with the spherical surface 25 of the spherical-cap joint 28 of the joint element 24.

Particularly in the case of cervical vertebrae it may be necessary to remove pathological deformations in the vicinity of an apophyseal ring. The removal of such deformations implies that the surgeon has to remove a larger part of an vertebra adjacent the intervertebral disc compartment. Such a removal increases the height of the intervertebral disc compartment. For example, if a larger portion of the lower part of the upper vertebra V1 has to be removed, this may be compensated with by replacing the joint element 24 of the upper constituent element 10 by a joint element 124 in which the spherical-cap face 125 is further away from the slide-in plate 126 of the joint element 124.

This design is shown in FIG. 16 in a representation similar to FIG. 15. It can be discerned therein that the two slide-in plates 126, 126' of the two joint elements 124, 124' are now situated further apart, in order to take account of the greater height of the intervertebral disc compartment. However, the joint element 124' of the lower constituent element 10' has remained unchanged in comparison with the design shown in FIG. 15.

From FIG. 16 it becomes clear that, although the spherical-cap face 125 is now further away from the slide-in plate 126, the position of the center of motion 180 has remained fixed with respect to the upper vertebra V1 at its optimal position which is anatomically predetermined.

Usually it is not possible for the surgeon to exactly estimate ahead of the implant surgery to which extent bone material of the adjacent vertebrae has to be removed. This usually becomes clear only during the surgery. The surgeon may then measure the height of the resulting intervertebral disc compartment, for example by using an adjustable template, and then determine at which position the supporting plates should abut the vertebrae. Additional spacers arranged between the vertebrae and the supporting plates may be provided. If the position of the supporting plates is determined, the surgeon selects a pair of slide-in plates having a geometry that ensures that the center of motion of the prosthesis coincides with the position of the anatomical center of motion which has been determined beforehand on the basis of 3D biometrical measurements.

FIG. 17 shows a situation in which, other as shown in FIG. 16, not a larger part of the upper vertebra V1 but a larger part of the lower vertebra V2 had to be removed. One way to compensate for this is to use an upper joint element 224 having a larger distance between the slide-in plate 226 and the spherical face 225. In order to keep the position of the center of motion 280 at its optimal anatomically determined position, this requires also to increase the radius of curvature of the spherical face 225. The radius r is then a given function r=r(a) of the distance a between the slide-in plate 226 and the spherical face 225. In this case both joint members 224, 224' are different as compared to the situation shown in FIG. 15.

FIG. 18 shows a combination of joint members 324, 324' that might be used instead of the joint members 224, 224' shown in FIG. 17. Here the radius of curvature of the spherical face 325 has not been increased. Instead, only the distance between the slide-in plate 326' and the spherical face 325' of the lower joint member 324' has been increased, similar to the situation shown in FIG. 16 for the upper joint member 124. Again, the center of motion 380 remains at the anatomically predetermined location in spite of the shifted positions of the abutment faces of the adjacent vertebrae V1, V2.

As an alternative to the exchange of joint members, the same effect can also be achieved by an exchange of the supporting plates having different thicknesses. This is due to the fact that what ultimately matters for the position of the center of motion is not the spacing of the spherical faces from the slide-in plates, but rather their spacing from the abutment faces of the adjacent vertebrae V1, V2. Therefore it might not even be necessary to exchange parts of the prosthesis as such if additional spacers of varying thickness are inserted between the abutment sides of the supporting plates and the adjacent vertebra. The spacers may have the shape of disks or wedges. A drawback of such spacers is that they have to be kept in place, and apart from that the intervertebral disc compartment is often too small to insert additional spacers.

By variation of the radii of curvature of the spherical-cap faces and/or of the spacings of the spherical-cap faces from the supporting plates it is therefore possible to adapt the intervertebral disc prosthesis to virtually any arbitrary geometry of intervertebral disc compartments whilst retaining the anatomically predetermined center of motion. If the surgeon is furnished with a kind of construction kit that comprises two supporting plates and a set of differently shaped joint elements, then by choice of the surgeon can perform the adaptation to the anatomically predetermined center of motion by making an appropriate choice of the joint elements.

Alternatively, the inserting joint elements may be specifically machined for a particular patient. This makes it possible to retain the center of motion even in those cases in which the vertebrae are very strongly pathological deformed, for example due to an accident. In this case the upper and lower constituent elements may each be machined as one-piece unit from a single block of a suitable material, e.g. titanium.

FIG. 19 shows an embodiment in which the center of motion 482 has been shifted in a longitudinal direction. This is accomplished by shifting the spherical faces 425, 425' of the slide-in plates 426, 426' relative to the base areas of these plates.

The same effect may be achieved by giving the spherical faces 525, 525' a shape that is not rotationally symmetric with respect to a central axis of the slide-in plates 526, 526'. Such an embodiment is shown in FIG. 20.

Figure 21:
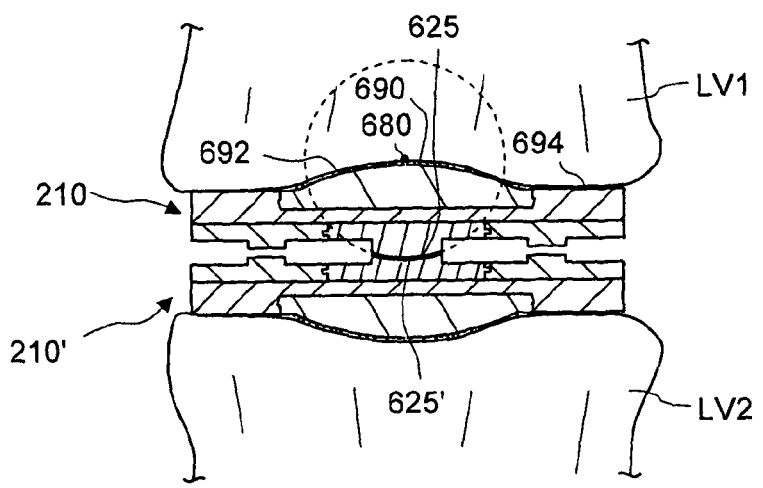
FIG. 21 is a side view of an intervertebral disc prosthesis according to another embodiment inserted between two lumbar vertebrae.

FIG. 21 shows, in a representation similar to FIG. 10, an intervertebral disc prosthesis constructed from two constituent elements 210, 210' in its position between two lumbar vertebrae LV1, LV2. The constituent elements 210, 210' differ from the constituent elements 10, 10' shown in FIGS. 1 to 11 only in that the spherical face 625 of the spherical-cap joint 628 and the spherical face 625' of the recess 625' have a larger radius of curvature. As a result, the center of motion 680 is positioned exactly in its anatomically optimum position, namely in the apex 690 of the dome 692 formed within the apophyseal ring 694 of the upper lumbar vertebra LV1.

Returning again to the first embodiment shown in FIGS. 1 to 11, it should be noted that the first and second guide plates 34, 36 on the transverse sides of the upper constituent element 10 make it possible to transfer the joint element 24 of the upper supporting plate 12 into its central position in the slide-in compartment 56 not only from the front via the third guide-plate slide-in compartment 62, but also from the side via one of the lateral guide-plate slide-in compartments 64, 66. Corresponding remarks also apply, of course, to the joint element 24' of the lower constituent element 10'.

In particular, it is possible to exchange the joint element 24 from the side even when the intervertebral disc prosthesis has already been inserted into the intervertebral disc compartment. The possibility of being able to exchange the joint element 24 from the side in this case is advantageous for the reason that a ventral access requires an access canal. However, creating such a canal for a second time is associated with increased risks. For instance, blood vessels that were displaced outwards through the ventral access canal in the course of the first operation may scar. As a result of the scarring, the blood vessels lose some of their elasticity, so that serious complications may occur if said blood vessels are displaced again in the course of a second operation. The creation of a lateral access canal is then the only possibility in order to be able to access an intervertebral disc prosthesis that has already been inserted.

Such an access may be necessary, for example, if it turns out that the intervertebral disc prosthesis was not optimally adapted to the center of motion and to the geometry of the intervertebral disc compartment. Furthermore, symptoms due to wear and tear of the joint elements may occur in rare cases, which impair the mobility of the intervertebral disc prosthesis.

In the following it will be elucidated, on the basis of FIGS. 22a to 22d, how in such a case the joint element 24 of the upper constituent element 10 can be exchanged via a lateral access. Corresponding remarks also apply, of course, to the joint element 24' of the lower constituent element 10'.

Figure 22A:
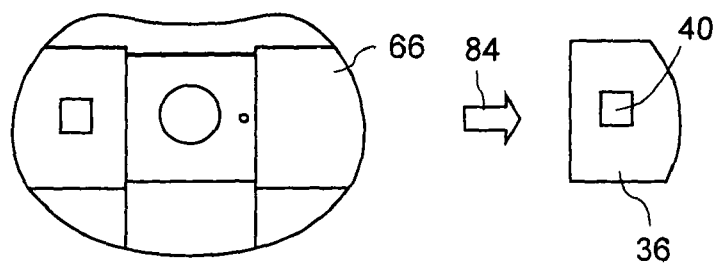
FIGS. 22a to 22d show the underside of the upper supporting plate in several states during the exchange of a joint element.
Figure 22B:
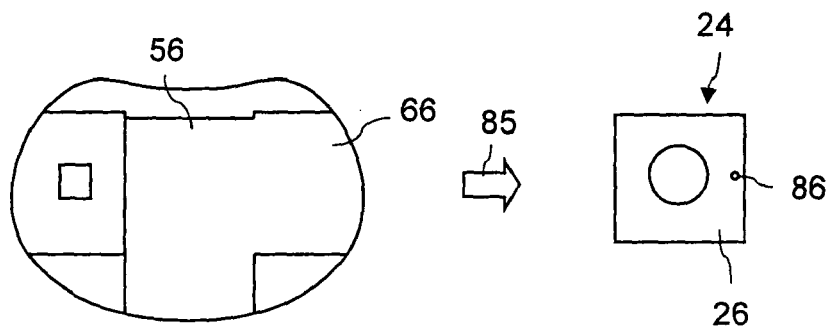

FIG. 22a shows, in a representation based on FIG. 6a, the underside of the upper supporting plate 12 pointing towards the lower constituent element 10'. Via a lateral access canal leading to the intervertebral disc compartment, firstly the second guide plate 36 is drawn out of the second guide-plate slide-in compartment 66, as indicated in FIG. 22a by an arrow 84. For this purpose, a wire loop, for example, can be placed around the projection 40 on the guide plate 36, with which the second guide plate 36 can be drawn out of the second guide-plate slide-in compartment 66. The second guide-plate slide-in compartment 66 which is now exposed reveals the lateral access to the joint element 24. The joint element 24 is now likewise drawn out via the second guide-plate slide-in compartment 66, as indicated in FIG. 22b by an arrow 85. For this purpose, the slide-in plate 26 of the joint element 24 may be provided with a bore 86. The surgeon is able to introduce a hook-shaped instrument into the bore 86, with which he/she draws the joint element 24 out laterally.

Figure 22C:
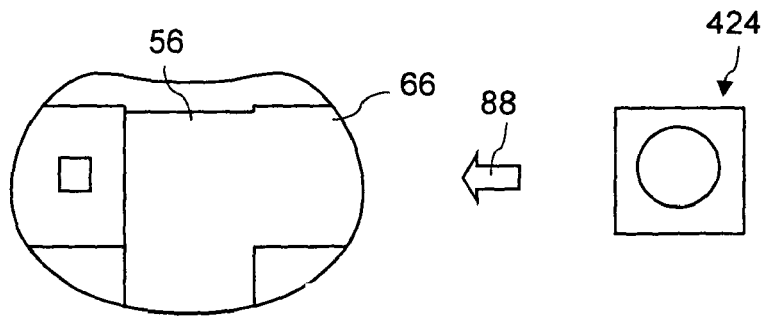
Figure 22D:
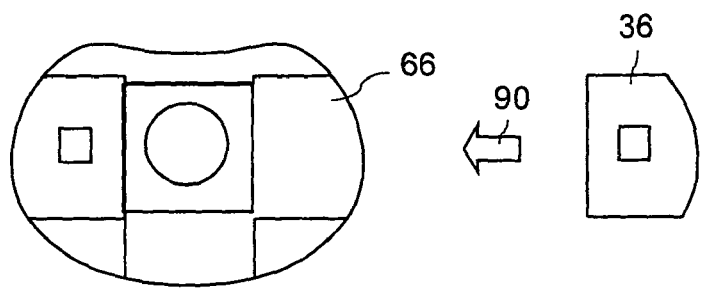

Another joint element 424 is now introduced again into the slide-in compartment 56, as indicated in FIG. 22c by an arrow 88. Finally, the second guide plate 36 is reintroduced into the second guide-plate slide-in compartment 66, as indicated in FIG. 22d by an arrow 90.

Of course, it is also possible, in the manner described above, to exchange not (only) the joint element 24 but (also) one or both guide plates 34, 36 via a lateral access, for example in order to fix the intervertebral disc prosthesis totally in the lateral direction, as shown in FIG. 12.

In order to keep the diameter of a ventral access canal small when the intervertebral disc prosthesis is being inserted, the supporting plates 12, 12' may firstly be introduced into the access canal with their transverse sides to the front, and may only be rotated into their definitive position within the intervertebral disc compartment or in the immediate vicinity thereof.

Figure 24:
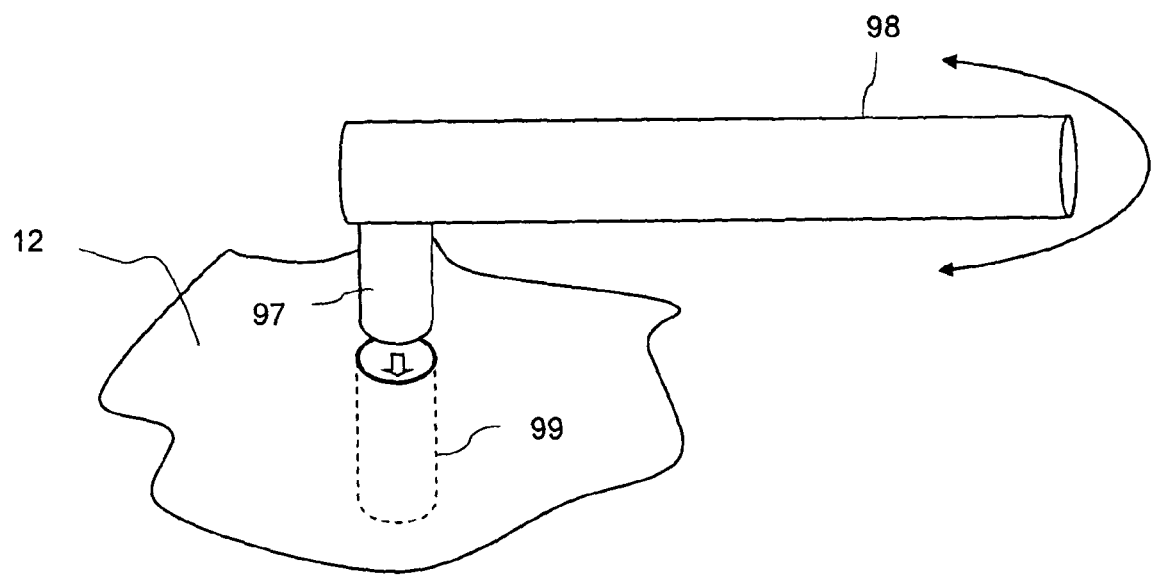
FIG. 24 is a perspective schematic representation of a connecting element for the operating rods.

This will be shown in the following with reference to FIGS. 23a, 23b and 23c, which in exemplary manner show the upper supporting plate 12 in top view. On the underside of the supporting plate 12 there are arranged connecting elements 94, 96, via which the upper supporting plate 12 can be connected separably and in articulated manner to operating rods 98, 100. The connecting elements 94, 96 may be realized as simple (pocket) bore into which the operating rods 98, 100 can be inserted. FIG. 24 shows an operating rod 98 which bears on one end a short peg 97 bent at an angle of about 90°. The diameter of the peg 97 is adapted to achieve a loose fit with a bore 99 provided in the first supporting plate 12. In this way, an easily separable and nevertheless articulated connection is obtained between the upper supporting plate 12 and the operating rods 98, 100.

The connecting elements 94, 96 are arranged at diagonally opposite corners of the upper supporting plate 12. If the upper supporting plate 12 is now connected to the operating rods 98, 100 via the connecting elements 94, 96, then as a result of moving the operating rods 98, 100 the upper supporting plate 12 can be rotated about an axis that extends perpendicular to a plane which is predetermined by the upper supporting plate 12.

If the operating elements 98, 100 are moved, for example in the direction indicated by arrows 104, 106, the upper supporting plate 12 rotates in the direction indicated by an arrow 108. This rotation is continued until such time as the upper supporting plate 12 attains the orientation shown in FIG. 23b. In this orientation the upper supporting plate 12 requires a ventral access canal, the diameter of which has to amount merely to d', where d' is the maximal width of the upper supporting plate 12. Indicated by d in FIG. 23b is the diameter of a ventral access canal such as would have to be created if the upper supporting plate 12 were to be introduced into the access canal not with its transverse side to the front but with its longitudinal side to the front.

Figure 23A:
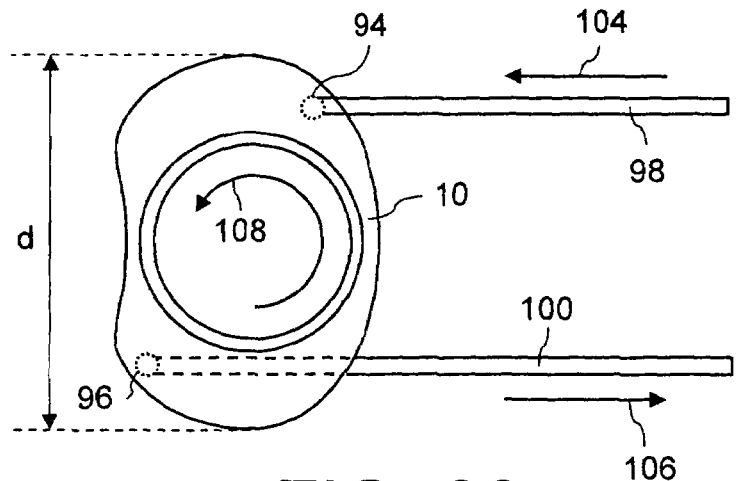
FIGS. 23a to 23c are top views of the upper supporting plate which is rotated with the aid of operating rods during its introduction into a ventral access canal.

As soon as the upper supporting plate 12 is located inside the intervertebral disc compartment, it is rotated back again into its position shown in FIG. 23a. For this purpose, the operating rods 104, 106 are moved in the direction indicated by arrows 110, 112, as a result of which the upper supporting plate 12 rotates in the direction indicated by an arrow 114 into the final position shown in FIG. 23c. The operating elements 98, 100 can now be separated from the connecting elements 94, 96 and drawn out of the ventral access canal.

Figure 25:
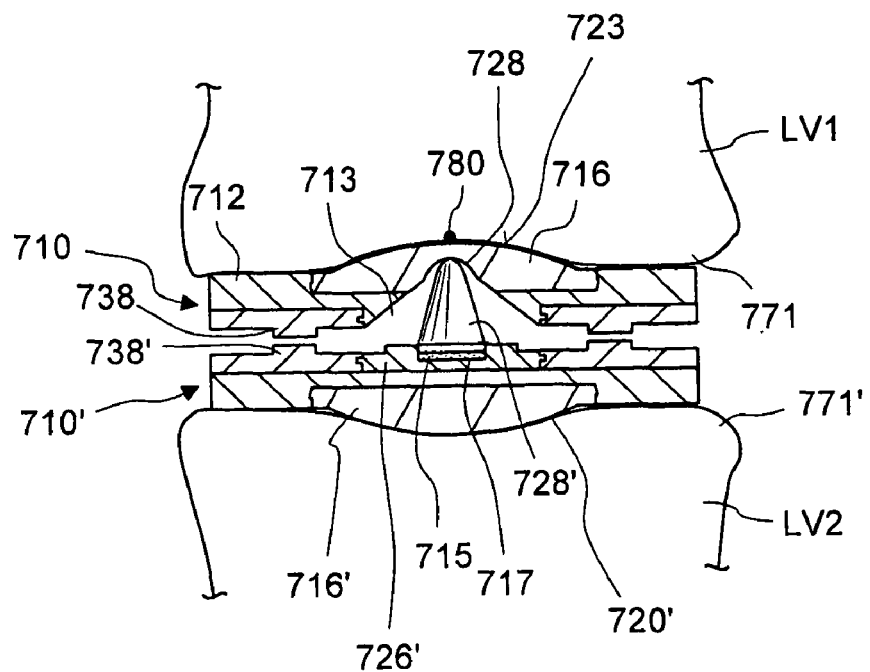
FIG. 25 is a side view of an intervertebral disc prosthesis according to a further embodiment inserted between two lumbar vertebrae in a first state.

FIG. 25 shows an intervertebral disc prosthesis according to another embodiment in a side view similar to FIG. 21. The prosthesis is inserted in an intervertebral disc compartment between two lumbar vertebrae LV1, LV2. In contrast to the embodiment shown in FIG. 21, the prosthesis has no ball-and-socket joint between two constituent elements 610, 610', but a needle joint comprising a recess 728 and a cone 728' having a rounded tip. The cone 728' thus has a shape similar to a sugar loaf.

The recess 728 is formed in a cap insert 716 of the upper constituent element 710. An upper supporting plate 712 is provided with a central opening 713, through which the tip of the cone 728' reaches into the recess 728.

The base of the cone 728' is fixedly received in a recess 717 formed in a slide-in plate 726' of the lower constituent element 710'. A disc-shaped damping element 715 made of an elastomer or another resilient material is sandwiched between a base of the cone 728' and a base of the recess 717.

Figure 26:
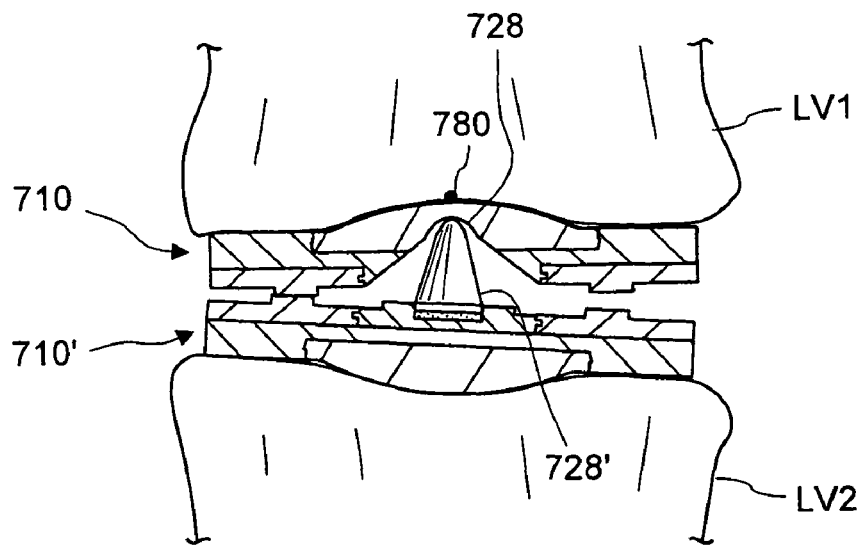
FIG. 26 shows the prosthesis of FIG. 25, but in a second state after swiveling the lower constituent element with respect to the upper constituent element.

The needle joint makes it possible to swivel the lower constituent element 710' around a swivel point which is situated in the apex of the recess 728 formed in the upper constituent element 710. FIG. 26 shows the intervertebral disc prosthesis of FIG. 25 in a state after swiveling the lower constituent element 710' by a few degrees. Since the recess 728 is formed within the cap 716 of the upper constituent element 710, the swivel point is in immediate vicinity to the anatomical center of motion indicated by a dot 780.

The embodiment shown in FIGS. 25 and 26 differ from the embodiments previously described further in that the external surface 720 of the cap insert 716 is not spherical. Instead, this external surface 720 is specifically adapted to the shape of the dome 723 formed between the apophyseal ring 771 of the upper vertebra LV1. To be more precise, the external surface 720 is formed as a complement part with respect to the dome 723, and there is no substantial gap between the external surface 720 on the one hand and the dome 723 on the other hand. Preferably, this gap has a width of less than 1 mm, at least over one half of the inner surface area of the dome 723.

Such an adaptation of the external surface 720 to the dome requires that the shape of the dome 723 is biometrically determined prior to the insertion of the intervertebral disc prosthesis into the intervertebral disc compartment. For determining the shape of the dome 723, high-resolution images of the upper vertebra L1 may be computer processed. The external surface 720 is then machined or molded in accordance with the obtained biometrical shape data of the dome 723.

Adapting the shape of the external surface 720 to the adjacent dome 723 has the advantage that the upper constituent element 710 is much more rigidly attached to the upper vertebra L1. Since the dome is not only aspherical, but usually also non-rotationally symmetrical, the cap insert 716, and thus the upper constituent element 710 as a whole, cannot rotate within the intervertebral disc compartment if there is a sufficient pressure exerted on the intervertebral disc prosthesis by the surrounding ligaments.

Further, there is no need to provide an additional rough coating that ensures a more intimate connection between the cap insert and the dome 723, as is the case in the embodiments previously described. Even more, it may be advantageous to polish the external surface 720 to reduce its roughness. This is because a smooth external surface 720 makes it possible that the cap insert 716, and thus the entire upper constituent element 710, adjusts itself with respect to the dome 723 by sliding movements when the intervertebral disc prosthesis is inserted into the intervertebral disc compartment. By exerting a slight longitudinal pressure, the constituent element 710 will slightly rotate around a longitudinal axis of the vertebrae VL1, VL2 until they reach a position in which a perfect match of the external surface 720 and the dome 723 is achieved.

Of course, the same considerations apply also to the lower cap insert 716' and its external surface 720'. It is further to be understood that specifically adapting the shape of the convexly projecting parts of the constituent elements of the intervertebral disc prosthesis may be advantageously used not only in connection with the present embodiment, but also with the other embodiments and quite generally with all prostheses having at least one convexly projecting part that reaches into the dome of an adjacent vertebra.

Figure 27:
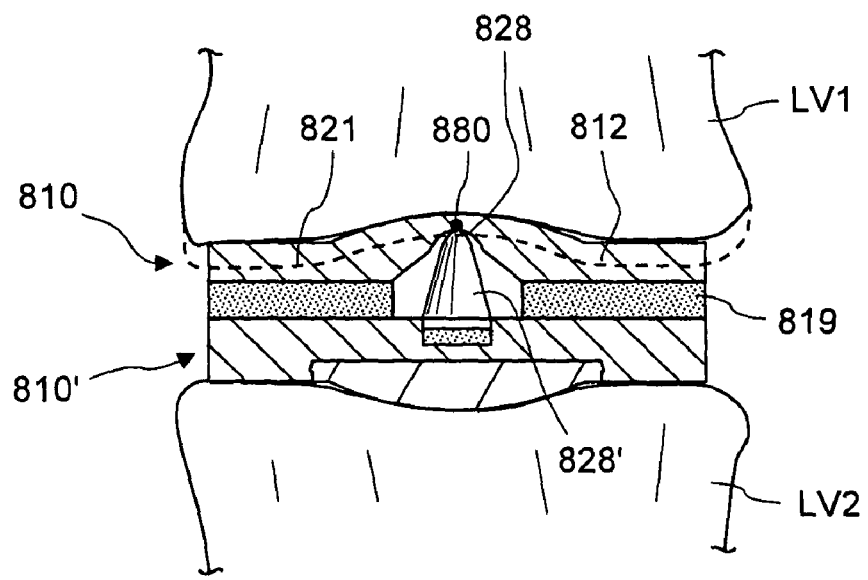
FIG. 27 is a side view of an intervertebral disc prosthesis according to a still further embodiment inserted between two lumbar vertebrae in a first state.
Figure 28:
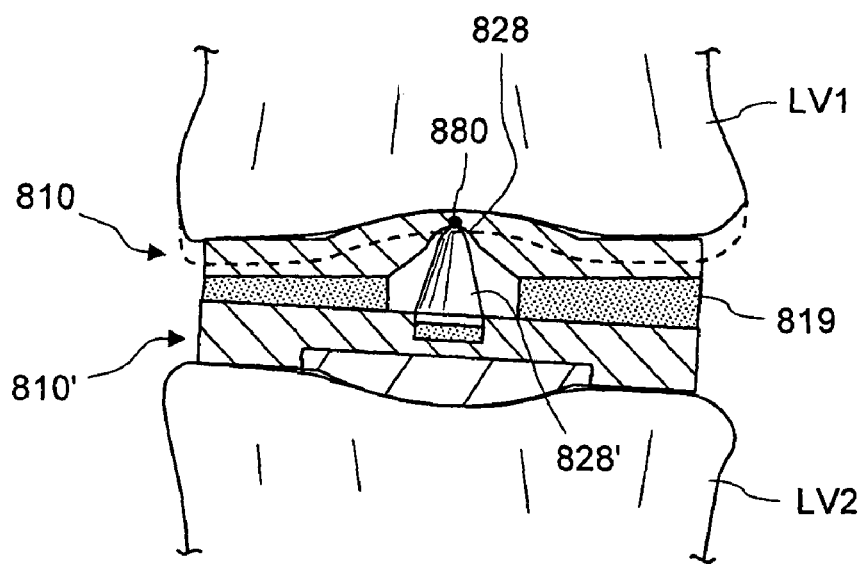
FIG. 28 shows the prosthesis of FIG. 27, but in a second state after swiveling the lower constituent element with respect to the upper constituent element.

FIGS. 27 and 28 show, in representations similar to FIGS. 25 and 26, still another embodiment of an intervertebral disc prosthesis in two different swiveling states. In this embodiment the space between the upper and lower constituent elements 810, 810' is filled with a ring-shaped damping disc 819 having resilient properties. The disc 819 is preferably stiff enough to carry some of the substantial forces that are present between the adjacent vertebrae LV1, LV2. On the other hand, the disc 819 has to be resilient enough to enable swiveling movements of the lower constituent element 810' with respect to the upper constituent element 810.

The disc 819 has therefore the advantage that, on the one hand, it reduces the forces exerted on the cone 828' and the recess 828, and on the other hand it provides for an efficient limitation of the swiveling movements. In comparison to the projections 738, 738' serving as a stop in the previous embodiment, the disc 819 ensures a smooth limitation of the swiveling movement, because the resilient forces increase with growing swiveling angles.

It can be further discerned in FIGS. 26 and 27 that the anatomical center of motion 880 is now positioned exactly in the apex of the recess 828. This is achieved by abrasing a part of the upper lumbar vertebra LV1 to an extent that is indicated in FIGS. 27 and 28 by a dashed line 821, which represents the shape of the upper lumbar vertebra LV1 prior to the abrasive process. The height of the removed bone volume corresponds, at least substantially, to the thickness of the supporting plate 812 above the apex of the recess 828. This height may be in the range between 1 mm and 5 mm and is preferably between 1.5 mm and 2.5 mm.

Figure 29:
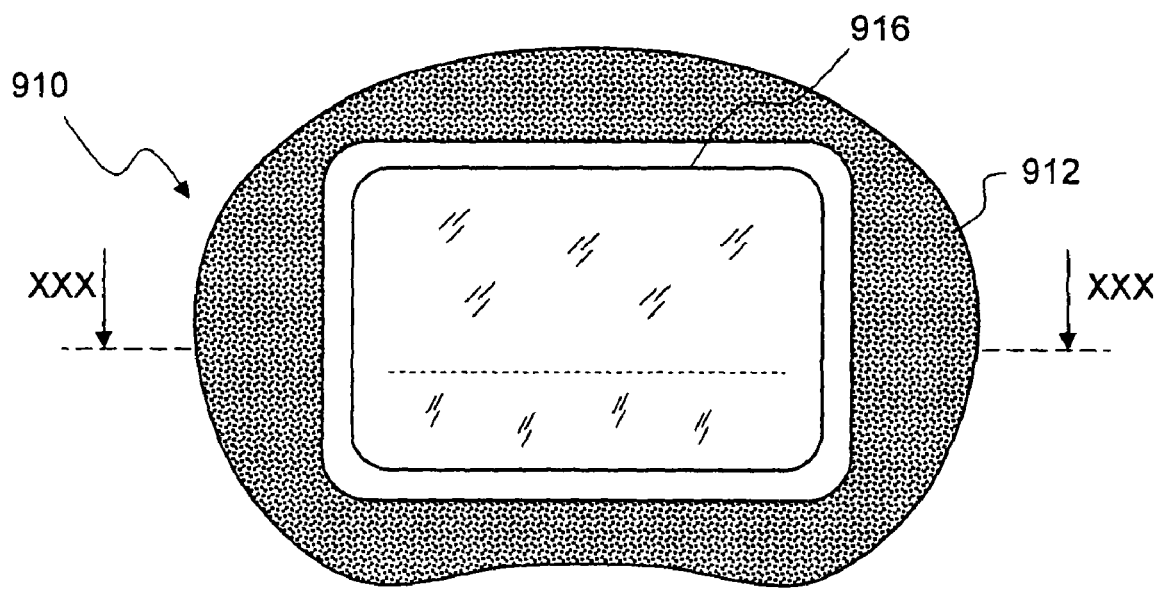
FIG. 29 is a top view of an upper constituent element of an intervertebral disc prosthesis according to another embodiment of the invention.
Figure 30:
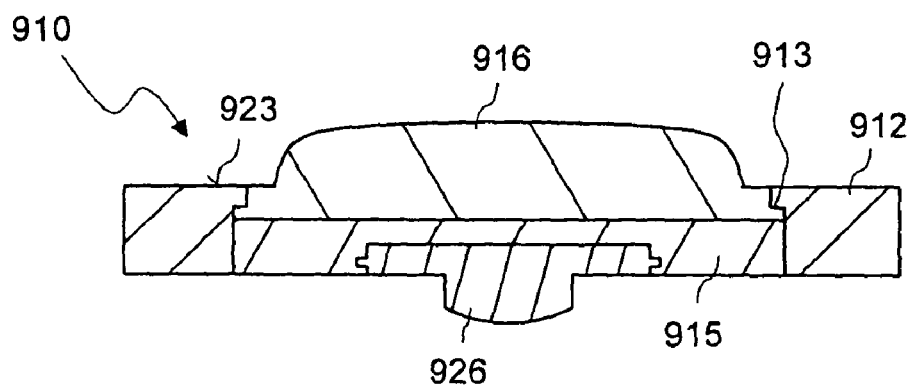
FIG. 30 is a section along line XXX-XXX of the upper constituent element shown in FIG. 29.

FIGS. 29 and 30 show an upper constituent element 910 of an intervertebral disc prosthesis according to still another embodiment in a top view and a section along line XXX-XXX, respectively. The upper constituent element 910 mainly differs from the other upper constituent elements described above in that it comprises a cap insert 916 having a shape that is specifically adapted to the recess within the apophyseal ring of the adjacent vertebra. More particularly, the cap insert 916 has a shape that is at least substantially complementary to this recess. This means that the gap between the cap insert 916 and the bone tissue between the apophyseal ring is very small, preferably not exceeding 1 or 2 mm. Preferably the largest part of the convex surface of the cap insert 916 is in direct contact to this bone tissue. However, this does not mean that the cap insert 916 has to bear the large forces exerted by the adjacent vertebrae. Instead, the upper constituent element 910 comprises a supporting plate 912 having a flat top annular area 923 on which the apophyseal ring of the adjacent vertebra rests. The supporting plate 912 is preferably made of a hard material having a rough surface.

In the embodiment shown, the upper constituent element 910 is assembled by inserting the cap insert 916 from below into the supporting plate 912 until it abuts on an annular projection 913. The cap insert 916 is then secured by means of a plate 915 which has a thread (not shown) on its circumference so that it can be screwed into the supporting plate 912. On the underside of the plate 915 a slide-in plate 926 with a convex spherical-cap joint is inserted in a similar way as shown in FIGS. 1 and 2.

Figure 31:
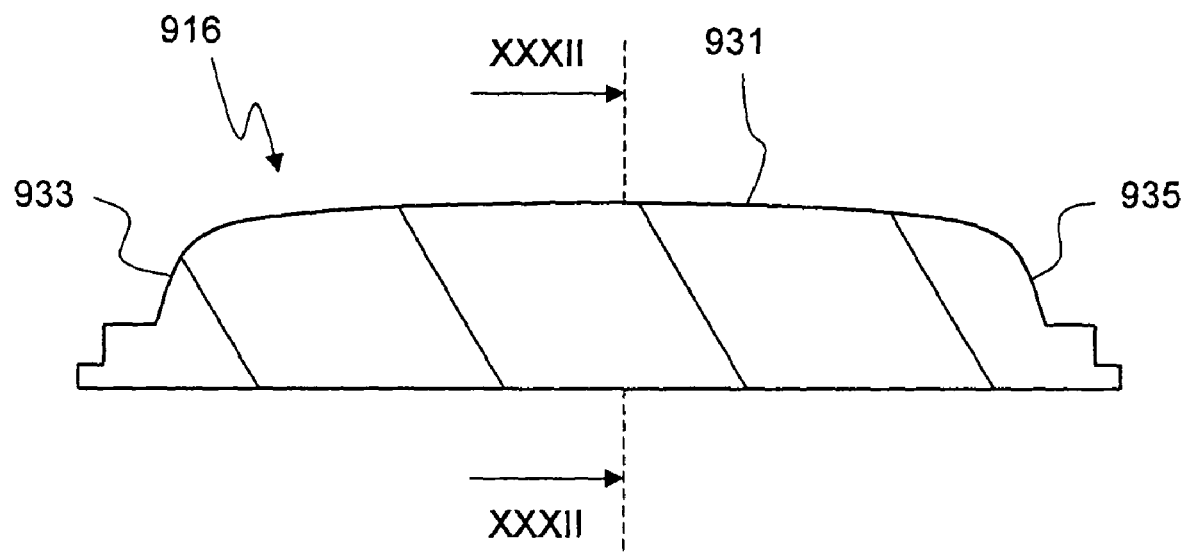
FIG. 31 is an enlarged section through a cap insert element of the upper constituent element shown in FIGS. 29 and 30.
Figure 32:
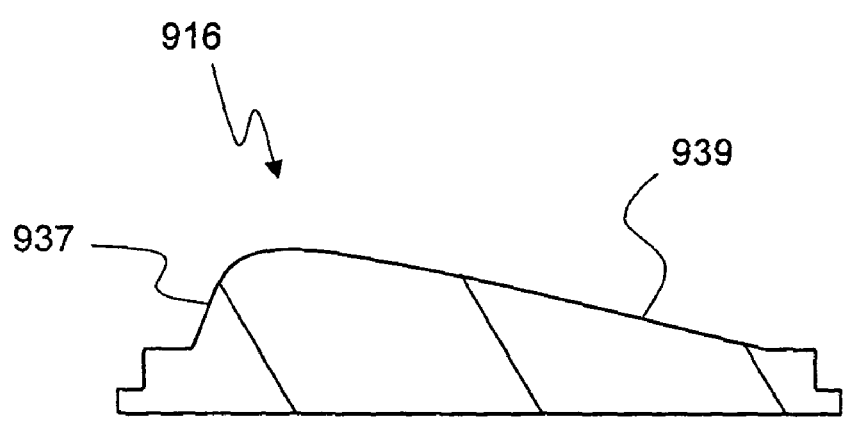
FIG. 32 is a section through the cap insert shown in FIG. 31 along line XXXII-XXXII.

FIGS. 31 and 32 show the cap insert 916 in an enlarged view and in a section along line XXXII-XXXII, respectively.

The cap insert 916 has, in a cross section along its longitudinal axis, a substantially horizontal section 931 centered between two inclined sections 933, 935. The cap insert 916 has, in a cross section along its transversal axis, a steeply inclined first section 937 and a less steeply inclined second section 939. This shape of a ramp corresponds to the shape of the dome formed between the apophyseal ring of the adjacent vertebra.

Figure 33:
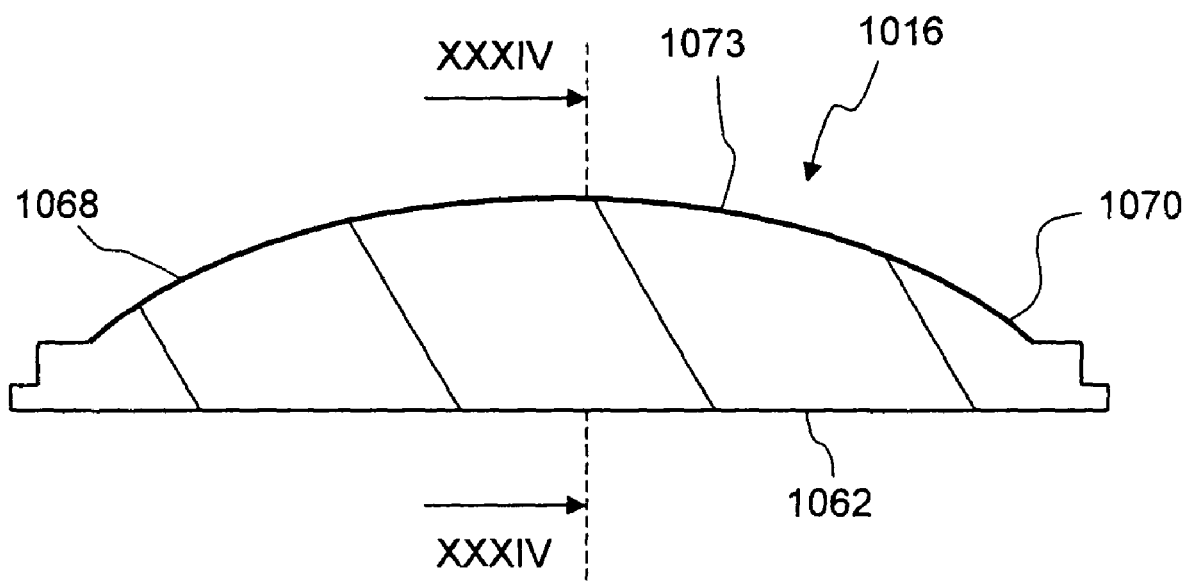
FIG. 33 is an enlarged section through a cap insert element according to another embodiment.
Figure 34:
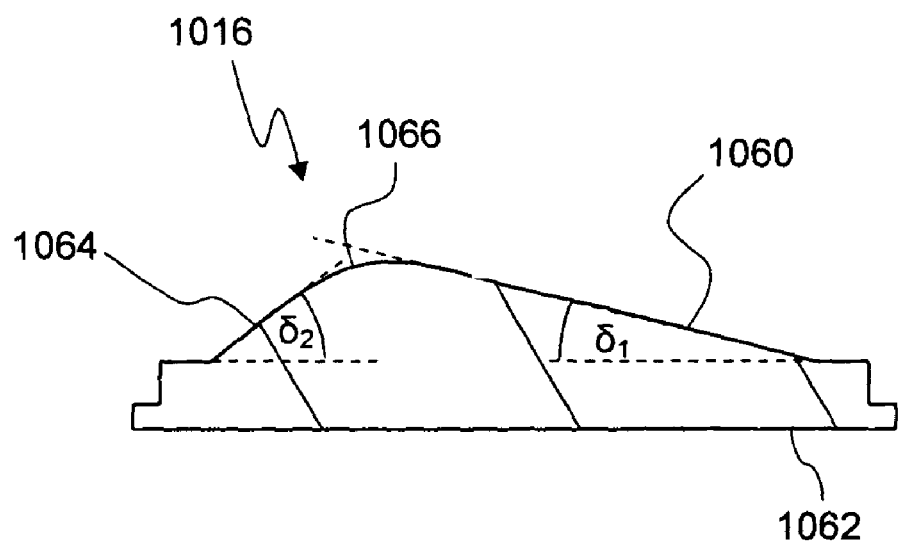
FIG. 34 is a section through the cap insert shown in FIG. 33 along line XXXIV-XXXIV.

FIGS. 33 and 34 show a cap insert 1016 according to another embodiment in illustrations similar to FIGS. 31 and 32, respectively. Again the convex region of the cap insert 1016 has the shape of a ramp similar to the embodiment shown in FIGS. 31 and 32. However, in this embodiment the convex region of the cap insert 1016 has a shape that slightly deviates from the shape of the dome between the apophyseal ring of the adjacent vertebra. This will be explained in more detail with reference to FIGS. 35a to 35c and 36a to 36c further below.

Returning back to FIGS. 33 and 34, the cap insert 1016 has a main flank 1060 which is inclined with respect to a base area 1062 by an main flank angle $\delta_1$ that may be, at least for most vertebrae, in a range between 5° and 20°. A counter flank 1064 is arranged opposite the main flank 1060 and forms a counter flank angle $\delta_2$ with the base area 1062. The counter flank angle $\delta_2$ may be, at least for most vertebrae, in a range between 25° and 50°. In the embodiment shown there is a transition area 1066 between the main flank 1060 and the counter flank 1064 which does not contain any edges and thus smoothly connects the main flank 1060 with the counter flank 1064. As can be seen in FIG. 33, the ramp of the cap insert 1016 has lateral sides 1068, 1070 that smoothly slope down towards the base area 1062.

The top surface of the cap insert 1016 is provided with a top coating 1073. The top coating 1073 should provide low friction relative to the soft bone material (substantia spongiosa) within the apophyseal ring of the adjacent vertebra. In an advantageous embodiment top coating 1073 is made of a diamond-like carbon (DLC). Such a coating can be applied using ion beam deposition or sputter deposition techniques to the surface of the cap insert 1016 and is not only biologically compatible, but is very hard and provides a smooth surface with very low friction. An arithmetic roughness Ra of less than 10 μm or even less than 1 μm may be easily achieved with such a coating 1073, which results in a very low friction to the adjacent bone material.

Instead of applying a low friction coating to the cap insert 1016, its surface may be polished by conventional methods. A polished surface of titanium, for example, also ensures very low friction values.

Figure 35A:
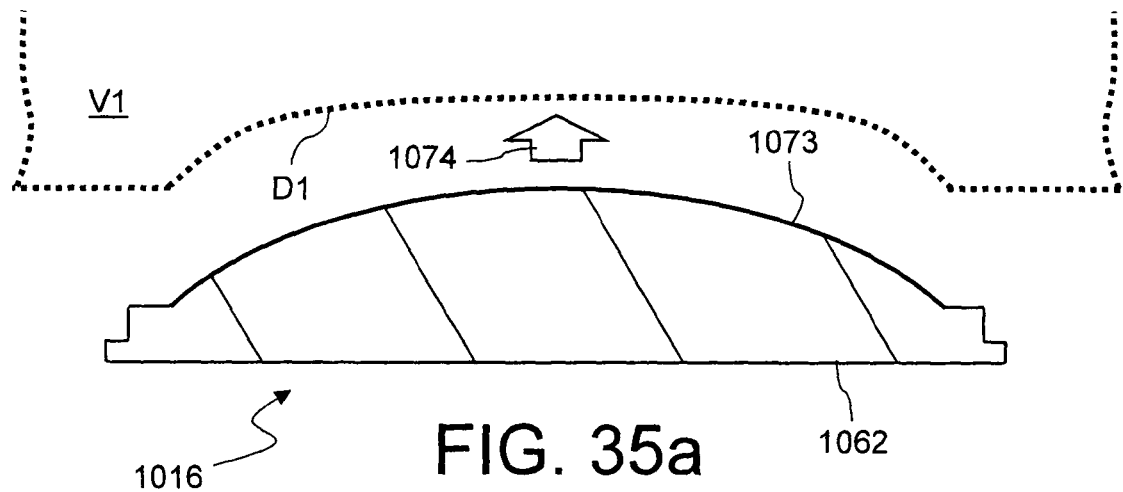
FIGS. 35a to 35c are cross sections through the cap insert shown in FIG. 33 and an adjacent vertebra in various constellations during the implant procedure.

FIG. 35a shows the cap insert 1016 in a section similar to FIG. 33 and the lower dome D1 of the adjacent upper vertebra V1 in the same section. As can be easily seen from FIG. 35a, the shape of the dome D1 slightly differs from the shape of the cap insert 1016.

Figure 35B:
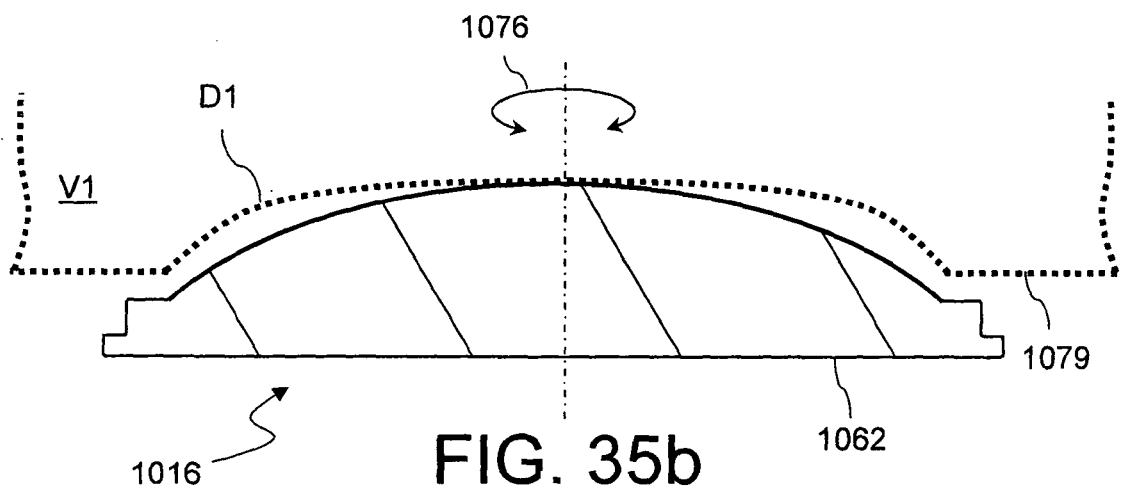

If the cap insert 1016 is inserted into the dome D1 of the upper constituent element 910 in a longitudinal direction indicated by an arrow 1074, only a small area in the vicinity of the vertex of the cap insert 1016 gets into contact with the vertex of the dome D1. This constellation is shown in FIG. 35b. As a result of the low friction coating 1073 applied to the surface of the cap insert 1016, the latter may easily be rotated by at least 10°, preferably by at least 25°, within the dome D1 until it has reached its final rotational position. The ability to rotate is denoted in FIG. 35b by a double arrow 1076. Easy rotatability is particularly important if the prosthesis is inserted through a narrow access canal with its longer dimension aligned along the canal axis. This even holds true for ventrolateral access canals because even there the constituent elements of the prosthesis have to be rotated by some 20° before they reach their final implant positioned.

Figure 23B:
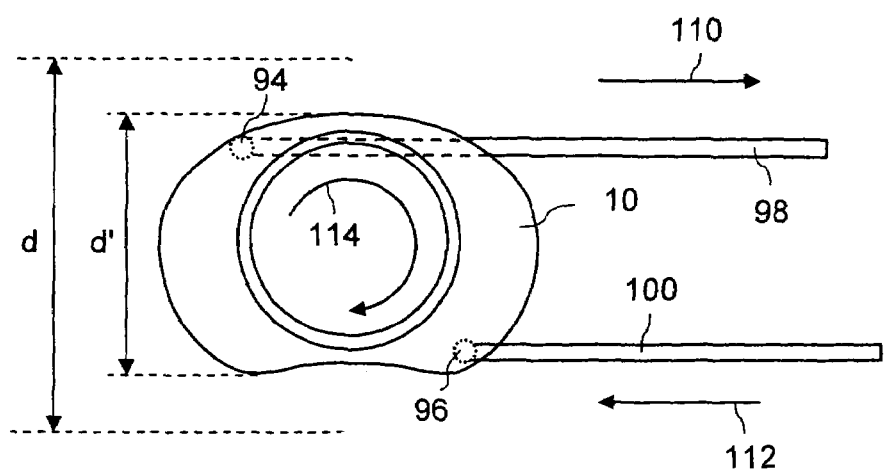
Figure 23C:
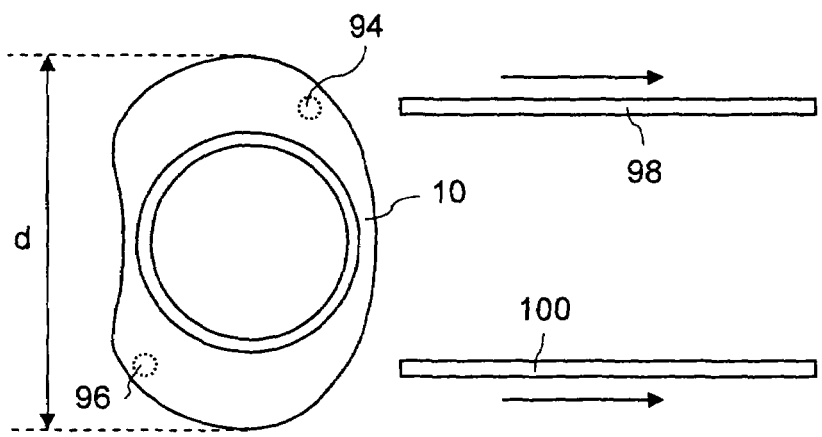

The rotation may be achieved by means of the rods 98, 100 shown in FIGS. 23a to 23c or by any other suitable means that are separably connectable to the upper constituent element 910. In certain cases no active manipulation at all, or a least no manual fine adjustment, is necessary because a self-centering effect occurs due to the low friction coating 1073 and the rotationally asymmetric shape of the dome D1 and the cap insert 1016. The term "self-centering effect" means that the cap insert 1016, and thus the entire upper constituent element 910, rotates if a compressive force is applied between the supporting plate 910 and the adjacent vertebra. During the implant surgery this force is produced by ligaments that extend along the spine. When the supporting plate has rotated to a position where these compressive forces are symmetrical, the torque causing the rotation vanishes, and the rotation ceases accordingly.

The self centering effect becomes very prominent if the kinetic friction coefficient observed between the coating 1073 and the dome D1 is as low as 0.1

Figure 35C:
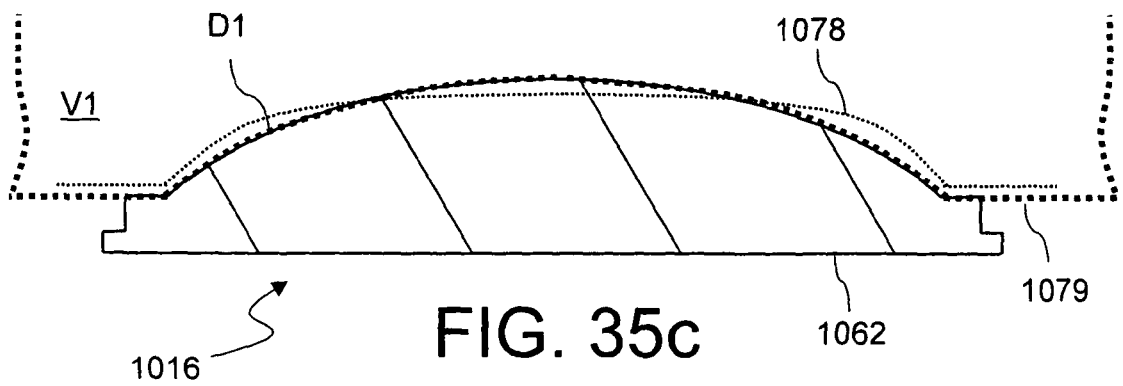

If the movement of the upper constituent element 910 along direction 1074 continues due to tension forces applied by ligaments to the adjacent vertebrae V1, V2, the vertex area of the cap insert 1016 that come first into contact with the dome D1 deforms the dome D1 by displacing some of the soft bone tissue (substantia spongiosa). This process continues until the hard apophyseal ring 1079 of the adjacent vertebra V1 rest on the annular area 923 of the supporting plate 912. This final constellation, in which a larger area or even the most part of the cap insert 1016 has intimate contact with the soft bone tissue (substantia spongiosa) of the upper vertebra V1, is shown in FIG. 35c. A thin dashed line 1078 indicates the shape of the dome D1 prior to its deformation by the cap insert 1016.

As a result of the rough surface of the annular area 923 and the intimate contact between a large part of the cap insert 1016 with the adjacent dome D1 the upper constituent element is rigidly fixed to the upper vertebra V1 so that no further fixing means like screws are required for maintaining the upper constituent element 910 in its final position.

Figure 36A:
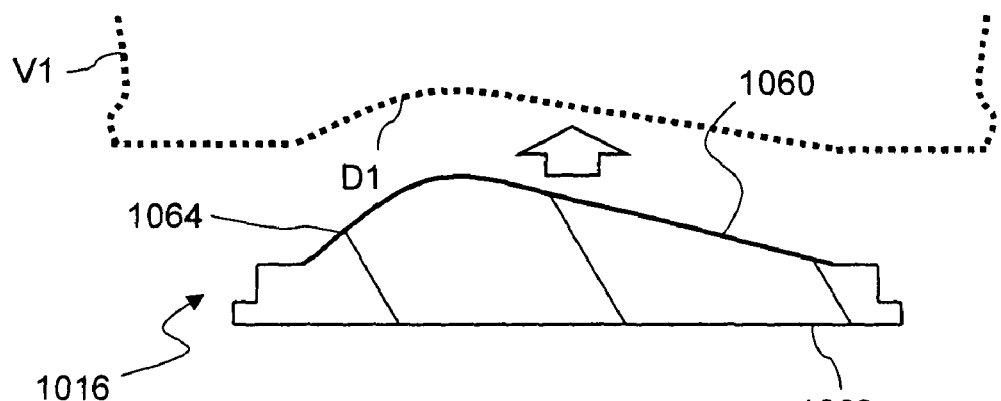
FIGS. 36a to 36c are cross sections through the cap insert shown in FIG. 34 and an adjacent vertebra in various constellations during the implant procedure.
Figure 36B:
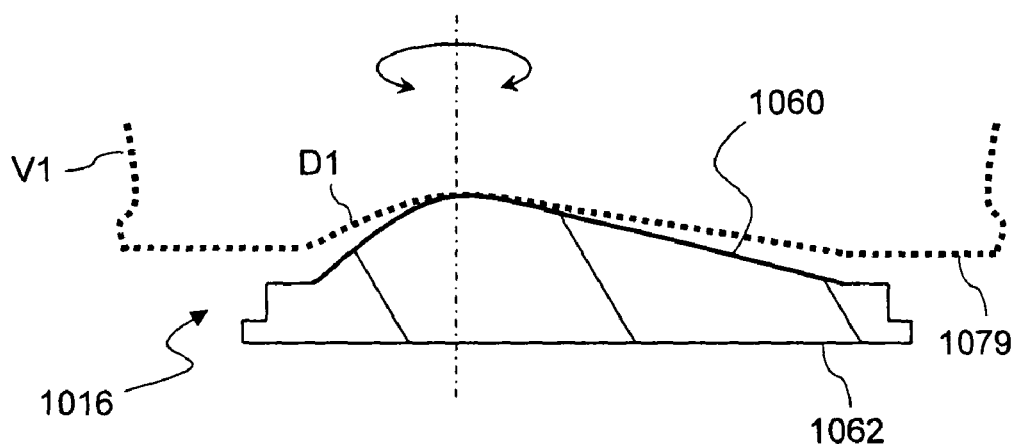
Figure 36C:
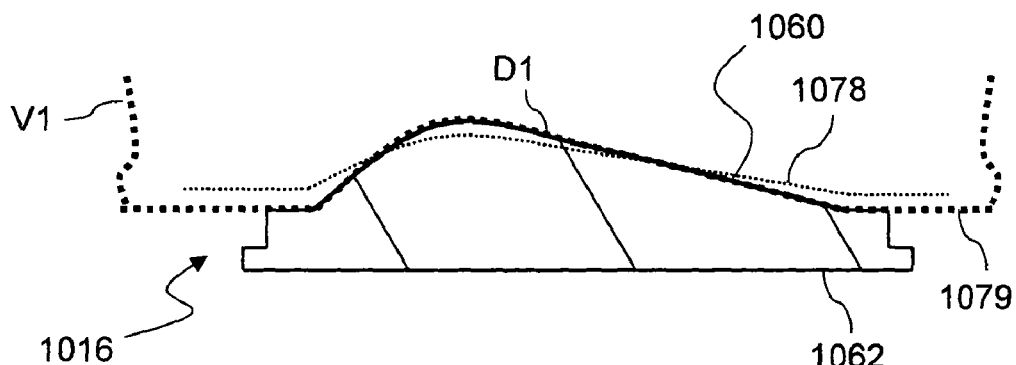
Figure 37:
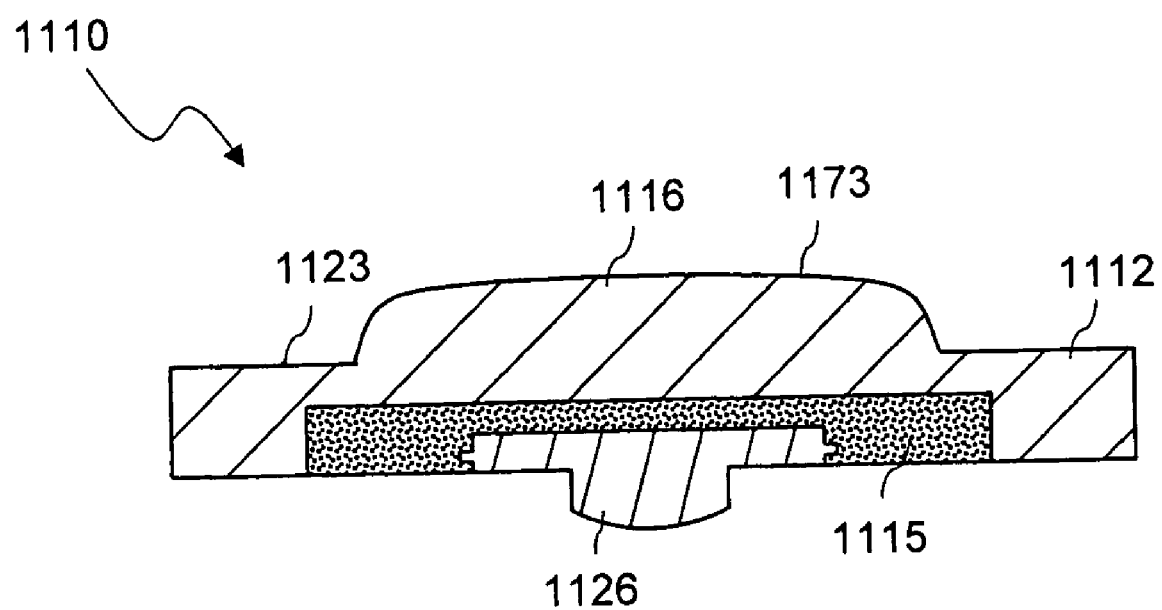
FIG. 37 is an enlarged section through a cap insert element according to still another embodiment.

FIGS. 36a to 36c show illustrations similar to FIGS. 35a to 35c, but for the cross-section as shown in FIG. 34.

Although the cap insert 1016 has a shape that slightly deviates from the shape of the dome D1, it may be advantageous to manufacture the cap insert 1016 individually for each vertebra on the basis of biometric data obtained for the particular patient. This ensures optimal rotatability on the one hand and a good intimate contact between the cap insert 1016 and the dome D1 on the other hand. However, since corresponding vertebrae of the human vertebral column often have similar shapes, it may suffice to provide the surgeon with a set of different cap inserts from which he selects one that suites best to the shape of the dome that has been biometrically determined beforehand.

In the embodiments described above it has been assumed that the cap insert is a separate part having different material and/or surface properties. However, the provision of a separate cap insert may also be advantageous with cap insert that are individually adapted to the patient's biometric data shall be manufactured. In this case only the individually manufactured cap inserts can be inserted into one or a few different supporting plates having the same standard recess for receiving the cap insert.

As a matter of course, it is also possible to manufacture supporting plates with integrated cap as a single piece. FIG.

37 shows, in a representation similar to FIG. 30, an upper constituent element 1110 having supporting plate 1112 with an integrated cap 1116. The surface 1173 of the cap 1116 is polished so that an arithmetic roughness Ra of less than 10 μm 0.1 is achieved, resulting in a kinetic friction coefficient of less than 0.1 with respect to soft bone material (substantia spongiosa).

In this embodiment a slide-in plate 1126 with a convex spherical-cap joint is received in a plate 1115 having elastic material properties. The material may have a modulus of elasticity of more than 1500 N/mm$^2$ which results in very good shock absorbing properties. Apart from the elastic plate 1115 also allows for translational movements of the slide-in plate 1126. As a result, the constituent elements of the prosthesis may, at least to a small extent, be translationally shifted relative to one another. The superposition of translational movements and of swivel movements provided by the ball-and-socket joint optimally reproduce the movements of healthy vertebrae of the vertebral column. It is to be understood that the provision of a plate 1115 having elastic material properties may also be advantageous in any of the other embodiments described above.

The above description of the preferred embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

The invention claimed is:

1. An intervertebral disc prosthesis for insertion into an intervertebral disc compartment which is formed between a first vertebra and a second vertebra, the prosthesis comprising:
   a) a first constituent element which
      comprises a first supporting plate, in which, on one side, a recess is formed and which has an annular flat region surrounding the recess and abutting against the first vertebra when the intervertebral disc prosthesis is inserted into the intervertebral disc compartment,
      comprises an insert which is received in the recess and which has a convexly curved region having at least substantially the shape of a ramp, and
      comprises a first joint member arranged on an opposite side of the first supporting plate, and
   b) a second constituent element which
      comprises a second supporting plate, in which, on one side, an abutment face is formed which abuts against the second vertebra when the intervertebral disc prosthesis is inserted into the intervertebral disc compartment, and
      comprises a second joint member arranged on an opposite side of the second supporting plate,
   wherein the convexly curved region has a long dimension in a first direction and a short dimension in a second direction orthogonal to the first direction,
   wherein the convexly curved region comprises, in a cross section perpendicular to the first direction, a first inclined section having a first incline and a second inclined section having a second incline smaller than the first incline, and
   wherein the convexly curved region has, in a cross section perpendicular to the second direction, a substantially horizontal section centered between two inclined third sections.

2. The intervertebral disc prosthesis according to claim 1, wherein the recess is formed by an opening provided in the first supporting plate.

* * * * *